United States Patent
Wu et al.

(10) Patent No.: US 12,054,560 B2
(45) Date of Patent: Aug. 6, 2024

(54) BIFUNCTIONAL MOLECULES RECRUITING ANTIBODIES AND TARGETING CANCER CELLS

(71) Applicant: JIANGNAN UNIVERSITY, Jiangsu (CN)

(72) Inventors: Zhimeng Wu, Jiangsu (CN); Zhifang Zhou, Jiangsu (CN); Haofei Hong, Jiangsu (CN)

(73) Assignee: JIANGNAN UNIVERSITY, Jiangsu (CN)

( * ) Notice: Subject to any disclaimer, the term of this patent is extended or adjusted under 35 U.S.C. 154(b) by 337 days.

(21) Appl. No.: 16/650,078

(22) PCT Filed: Dec. 29, 2017

(86) PCT No.: PCT/CN2017/119779
§ 371 (c)(1),
(2) Date: Mar. 24, 2020

(87) PCT Pub. No.: WO2019/127346
PCT Pub. Date: Jul. 4, 2019

(65) Prior Publication Data
US 2021/0198381 A1   Jul. 1, 2021

(51) Int. Cl.
*C07K 16/44* (2006.01)
*A61K 47/60* (2017.01)
*A61K 47/65* (2017.01)

(52) U.S. Cl.
CPC .............. *C07K 16/44* (2013.01); *A61K 47/60* (2017.08); *A61K 47/65* (2017.08)

(58) Field of Classification Search
None
See application file for complete search history.

(56) References Cited

U.S. PATENT DOCUMENTS

2012/0034295 A1* 2/2012 Spiegel ................ A61K 47/68
424/450
2014/0249296 A1* 9/2014 Ploegh ................... C12N 9/52
435/68.1

FOREIGN PATENT DOCUMENTS

| CN | 101856497 A | 10/2010 | | |
|---|---|---|---|---|
| CN | 105017340 A | 11/2015 | | |
| CN | 106146824 A | 11/2016 | | |
| WO | WO-2013155526 A2 | * 10/2013 | ....... | A61K 47/48561 |
| WO | WO-2015042393 A2 | * 3/2015 | ........... | C07K 14/473 |

OTHER PUBLICATIONS

Murelli et al., J Am Chem Soc 131: 17090-17092 (Year: 2009).*
Lloyd et al., Protein Engineering, Design & Selection 22:159-168 (Year: 2009).*
Edwards et al., J Mol Biol. 334(1): 103-118 (Year: 2003).*
Gray et al., Chembiochem 17: 155-158 epublished (Year: 2016).*
Oliveira et al., Molecular Imaging 11(11): 33-46 (Year: 2012).*
Parthasarathy et al., Bioconjugate Chem 18: 469-476 (Year: 2007).*
Xu et al., International J of Molecular Sciences 18: 2284 (Year: 2017).*
Tsukiji et al., ChemBioChem 10: 787-798 (Year: 2009).*
International Search Report dated Aug. 10, 2018 for related PCT/CN2017/119779 filed Dec. 29, 2017.
Written Opinion dated Aug. 10, 2018 for related PCT/CN2017/119779 filed Dec. 29, 2017.

* cited by examiner

*Primary Examiner* — Phuong Huynh
(74) *Attorney, Agent, or Firm* — MagStone Law, LLP; Enshan Hong

(57) ABSTRACT

The present invention belonging to the technical field of biopharmaceutical discloses bifunctional molecules which are used to recruit antibodies and target tumor cells. The bifunctional molecules in the present invention comprise at least one recruitment moiety capable of binding to the existing antibodies in the body and a targeting moiety capable of selectively binding to the tumor cell. The compounds according to the invention selectively bind to the surface of the cancer cells, and recruit the existing antibodies through the recruitment moiety, and mediate the humoral and cellular immune responses to the cancer cell in the patient. According to this physiological function of the compounds according to the invention, cancer cells can be immunoregulated, which provides a new strategy for tumor immunotherapy.

3 Claims, 11 Drawing Sheets
Specification includes a Sequence Listing.

BIFUNCTIONAL MOLECULES RECRUITING ANTIBODIES AND TARGETING CANCER CELLS

RELATED APPLICATIONS

This is a U.S. national stage of international application No. PCT/CN2017/119779 filed on Dec. 29, 2017.

SEQUENCE LISTING

The instant application contains a Sequence Listing which has been submitted electronically in ASCII format and is hereby incorporated by reference in its entirety. Said ASCII copy, created on Sep. 27, 2022, is named Sequence-2022-09-14, and is 4,807 bytes in size.

BACKGROUND OF THE INVENTION

1. Technical Field

The present invention relates to the field of biomedical or biopharmaceutical technology, and more specifically to the bi-functional molecules cable of binding target cells and recruiting antibodies.

2. Background Art

Recent decades have witnessed the significant increase of morbidity and mortality of cancer. In 2015, there was approximately 4 million new cancer suffers in China, and 2.8 million cancer patients died. Due to the drawbacks including low specificity and high side effects of traditional treatments, one effective way is to enhance the binding specificity and decrease the side effects of anti-cancer drugs.

Currently, monoclonal antibodies are the most popular anti-cancer drugs in the market, such as the Rituximab is successfully used for Hodgkin's Lymphoma treatment. However, the huge molecular weight (150 kDa) and high production cost may limit the anti-cancer efficacy and further application of monoclonal antibodies. This led to the development of the fragments with smaller molecular weight, including Fab fragments and scFv fragments. Nevertheless, the stability and binding affinity of these fragments remains inadequate compared with conventional monoclonal antibodies.

Therefore, it is to rationally screen or design smaller antigen-binding molecules with high stability and binding affinity. Among which, nanobodies (VHH) and some peptide motifs (such as RGD peptide) have shown superior characters.

On the other hand, to alleviate the problems caused by side effects and drug resistance, one promising strategy is to elicit or amplify endogenous immune response to kill diseased cells. Among which, the antibody-recruitment strategy is based on: 1) utilization of haptens could bind nature occurring endogenous antibodies, such as DNP, α Gal, Rha or PC; 2) utilization of antibody-binding domain such as ZZ domain to recruit endogenous antibodies on target cells for immune system activation, resulting in target cell disruption.

In addition, how to design and obtain antibody-recruit domain and cell-binding domain conjugates is still a question need to be investigated.

SUMMARY OF THE INVENTION

Based on the above-described tumor-targeting molecular and antibody-recruitment molecular strategy, the present invention has developed a series of pharmaceutical compounds containing different linkers to use in immunotherapy of tumors.

The first purpose of the present invention is to provide a series of nanobody-based antibody recruitment bi-functional molecules for tumor immunotherapy, the bi-functional molecule having the structural formula shown in Formula 1,

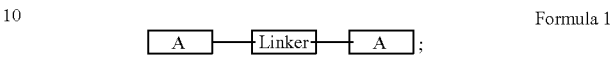

Formula 1

Wherein, A is a structure capable of recruiting antibody, including hapten, polypeptides, Z/ZZ domain affinity peptides, and analogues of these compounds which are capable of binding to antibody; and B is a substance capable of binding to a cell surface, including fragments having antibody function which is not limited to oligopeptides, polypeptides, nanobodies or fragments having antibody function; Linker is a linking structure linking A and B, which is not limited to chemical bonds or molecular linkers.

In one embodiment of the invention, A is a hapten structure which is capable of binding to an antibody existing naturally in the human body.

In one embodiment of the present invention, the naturally existing antibodies in the human body include groups, which are not limited to DNP and Rha groups.

In one embodiment of the present invention, B is RGD and a derivative thereof, which is not limited to RGD cyclic peptide; Said RGD is arginine-glycine-aspartate.

In one embodiment of the present invention, B is NGR and a derivative thereof, said NGR is asparagine-glycine-arginine.

In one embodiment of the present invention, B is LHRH and a derivative thereof, said LHRH is a luteinizing hormone-releasing hormone.

In one embodiment of the present invention, B comprises a nanobody against a tumor cell epidermal growth factor receptor EGFR, a nanobody against HER2, a nanobody against a prostate specific membrane antigen (PSMA), or a fusion protein of the above nanobody with a Z(ZZ) domain.

In one embodiment of the present invention, Ain the bi-functional molecule comprises two different haptens or a Z/ZZ domain affinity peptide.

In one embodiment of the present invention, the structural formula of the bi-functional molecule is:

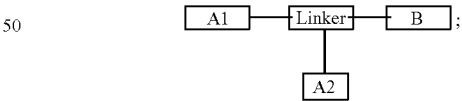

Wherein, A1 and A2 are two different hapten structures capable of binding to the naturally existing antibodies in the human body; B contains tumor-targeting nanobodies; Linker is a linking structure linking A and B, which is not limited to chemical bonds or molecular linkers.

In one embodiment of the present invention, the naturally existing antibodies in the human body include groups, which are not limited to DNP and Rha groups.

In one embodiment of the present invention, B comprises a nanobody against a tumor cell epidermal growth factor receptor EGFR, a nanobody against HER2, a nanobody against a prostate specific membrane antigen (PSMA), or a fusion protein of the above nanobody with a Z(ZZ) domain.

In one embodiment of the present invention, B is linked to the linker by a sortase A enzyme.

In one embodiment of the present invention, B with LPXTGn and a linker with Gn are connected by sortase A.

In one embodiment of the present invention, the structural formula of the linker is

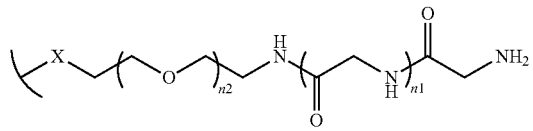

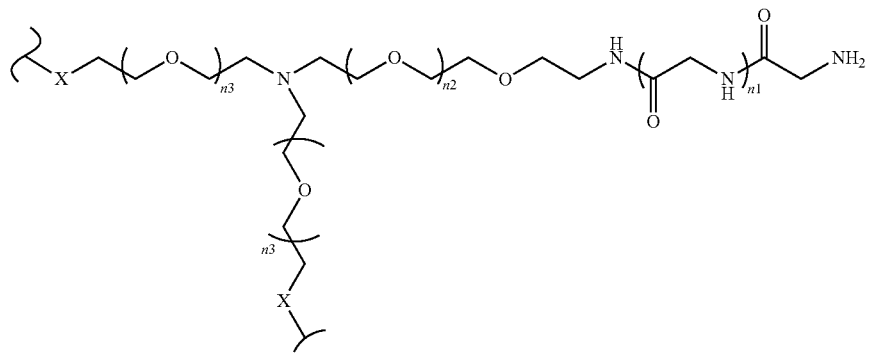

or LPXTGn-; The -LPXTGn- is -leucine-valine-X-threonine-n glycine; wherein n is an integer from 1 to 10; n1 is an integer from 1 to 4; n2 is an integer from 2 to 9; n3 is an integer from 2 to 9; X is O or S or N.

In one embodiment of the present invention, near the X-terminus of

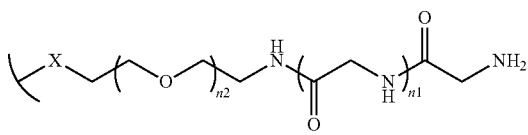

is a hapten structure, B at the other terminus is linked by SortaseA.

In one embodiment of the present invention, near the X-terminus of

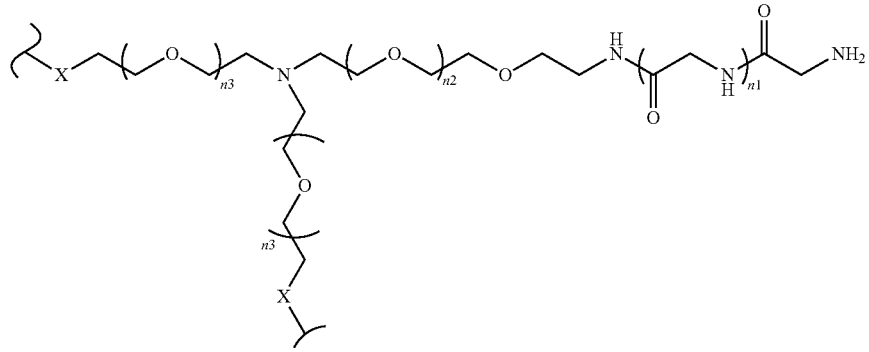

is the same or a different hapten, B at the other terminus is linked by SortaseA.

-LPXTGn- is suitable for SortaseA to directly link the nanobody to the Z(ZZ) domain, which is ligated to the N-terminus or C-terminus of the Z/ZZ domain.

In one embodiment of the invention, the structural formula of the bi-functional molecule is:

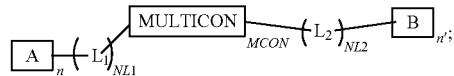

Wherein A is an antibody-binding terminus which is a hapten structure capable of binding to an existing antibody in a patient; B contains a nanobody capable of binding to cells; L1 and L2 are a linker and contain one or more bi-functional linker groups CON; MULTICON is bi-functional or poly-functional linker group, when MCON≥1, MULTICON connects at least one A to B via a linker L1 and/or L2;

MCON is an integer 0-10; N and N' are each independently an integer from 1 to 15, usually from 2 to 10, usually from 2 to 5, more usually from 2 to 3, or 2, 3, 4, 5 or 6; NL1 and NL2 are each an integer of 0 to 10, and n≥NL1, and n'≥NL2.

In one embodiment of the present invention, the MCON is 1, 2 or 3.

In one embodiment of the present invention, the MCON is 1.

In one embodiment of the present invention, n is 1, 2 or 3 and n' is 1 or 2.

In one embodiment of the present invention, NL1 is 1 and NL2 is 1.

In one embodiment of the present invention, MCON is 0, NL1 is 1 and NL2 is 1.

In one embodiment of the present invention, MCON is 0, n is 1 and n' is 1.

In one embodiment of the present invention, NL1 is 1.

In one embodiment of the present invention, NL2 is 1.

In one embodiment of the present invention, the B comprises an immunoglobulin single variable domain, or nanobodies, or polypeptides and derivatives thereof which can bind to a cells surface target; The polypeptide and its derivatives can target to cells surface target.

In one embodiment of the present invention, the polypeptide of B can be targeted to bind to cells surface target; Said cells are diseased cells, which are not limited to a cancer cell.

In one embodiment of the present invention, the structure of B is:

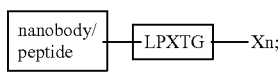

Wherein X is any amino acid and a derivative thereof, the -LPXTGn- is -leucine-valine-X-threonine-n glycine; X is O or S or N; n is an integer from 1 to 100.

In one embodiment of the invention, the bi-functional linker groups CON include:

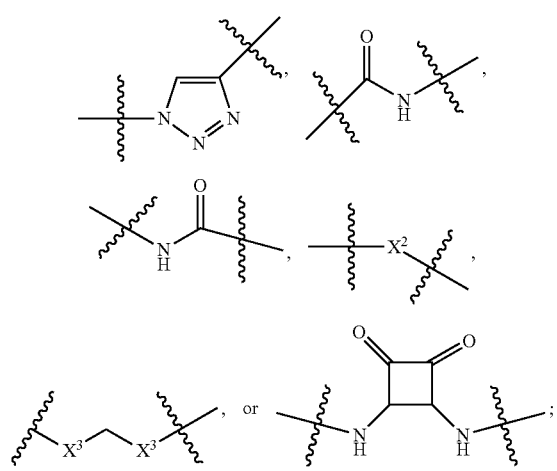

Wherein X2 is O, S, NR4, S(O), S(O)2, —S(O)2O, —OS(O)2 or OS(O)2O; X3 is O, S, NR4; R4 is a H, C1-C3 alkyl or alkanol group, or a —C(O)(C1-C3) group; or a pharmaceutically acceptable salt form thereof.

In one embodiment of the present invention, the bi-functional linker group CON is

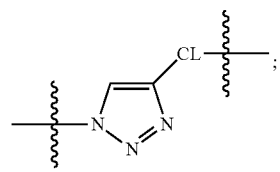

Wherein CL is

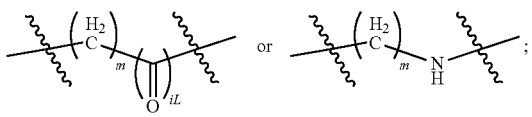

m is an integer from 0 to 12, typically 0, 1, 2, 3, 4, 5, 6; and IL is 0 or 1, usually 1.

In one embodiment of the present invention, the linker L1 or L2 comprises a polyethylene glycol (PEG) linker, a polypropylene glycol linker or a polyethylene glycol-co-polypropylene polymer, the length of which is from 1 to 100 units.

In one embodiment of the present invention, the linker L1 or L2 is a polyproline linker or a collagen linker: wherein the structural formula of the polyproline linker is

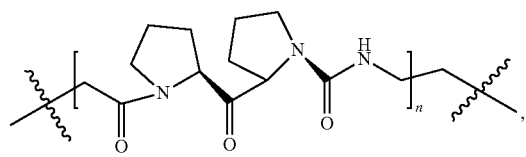

the structural formula of the collagen linker is

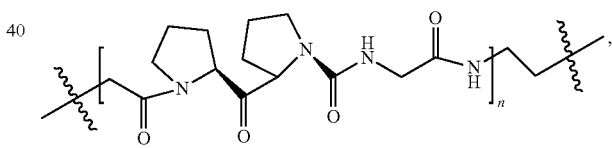

wherein n is from 1 to 100.

In one embodiment of the present invention, the linker L1 or L2 is

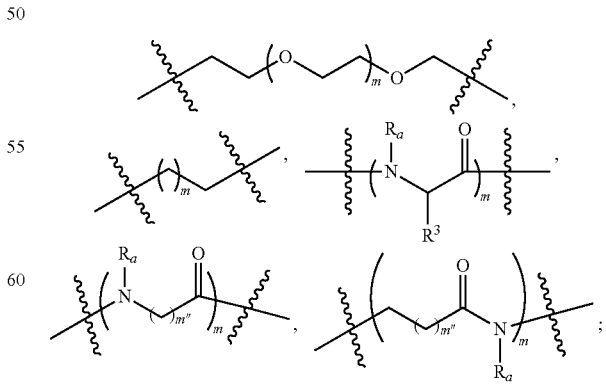

Wherein, Ra is H, a C1-C3 alkyl or alkanol or forms a ring with R3, R3 is a side chain derived from an amino acid; m is an integer from 1 to 100; and m" is an integer from 0 to 25. Any of the above groups can be further linked by an amide group, a ketone group, an amine group or an amino acid.

In one embodiment of the present invention, the linker L1 or L2 is

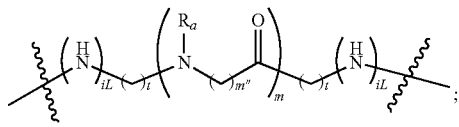

Wherein, Ra is H or a C1-C3 alkyl group, usually CH3, most usually H; m is an integer from 1 to 12, usually 1, 2, 3, 4, 5 or 6; m" is an integer 1, 2, 3, 4, 5 or 6, usually 6; t is 1, 2, 3, 4, 5 or 6; and iL is 0 or 1, wherein the linker is optionally attached to the A group at one terminus, and optionally attached to the B group at the other terminus.

In one embodiment of the present invention, the linker L1 or L2 is

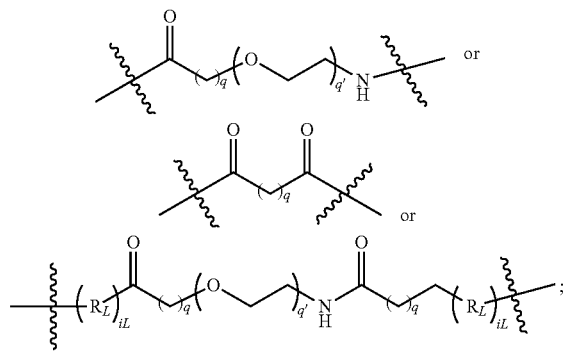

wherein q is an integer from 0 to 12; and q' is from 1 to 12; RL is 0 or 1; and RL is an amino acid or an oligopeptide;

Or a linker succinimide according to the following chemical structure:

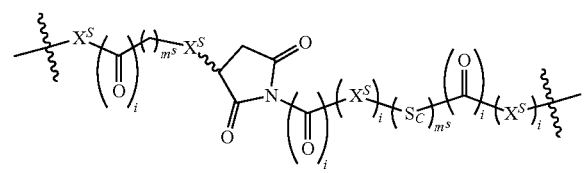

Wherein each XS is independently S, O or N—RS; RS is H or C1-C3 alkyl; SC is CH2, CH2O or CH2CH2O; i is 0 or 1; and ms is 0, 1, 2, 3, 4, 5 or 6;

Or a linker according to the following chemical formula:

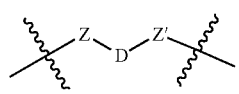

Wherein Z and Z' are each independently a bond, including —(CH2)iS, —(CH2)iNR;

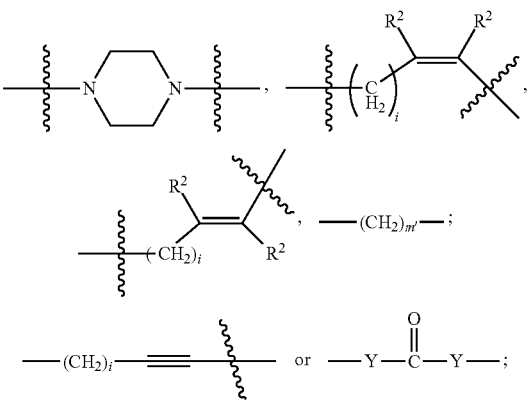

or optionally attached to another linker group, linker, group A or group B; each R is H, or an alkyl or alkanol group; each R2 is independently H or alkyl; each Y is independently a bond, O, S or N—R; each i is independently from 0 to 100;

D is

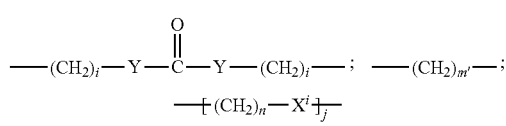

or bonds, or

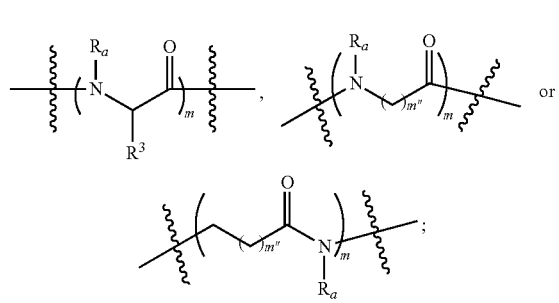

or a polypropylene glycol or polypropylene-co-polyethylene glycol linker having 1 to 100 diols; wherein Z, Z' and D are each not a bond; each i is independently from 0 to 100; j is from 1 to 100; m is an integer from 1 to 100; and n is an integer from 1 to 100; m" is from 1 to 100; m" is an integer from 1 to 25; usually from 1 to 10, usually from 1 to 8; more usually 1, 2, 3, 4, 5 or 6; n' is an integer from 1 to 100, or from 1 to 75, or from 1 to 60, or 1-5 from 1 to 5, or from 1 to 50, or from 1 to 45, or from 1 to 40, or from 2 to 35, or from 3 to 30, or from 1 to 15, or from 1 to 10, or from 1 to 8, or from 1 to 6, or 1, 2, 3, 4 or 5; Xi is O, S or NR; R is H, or an alkyl or alkanol group; Ra is H, a C1-C3 alkyl or alkanol or forms a ring with R3, R3 is a side chain derived from an amino acid; or a pharmaceutically acceptable salt form thereof, solvate or polymorph.

In one embodiment of the present invention, the bi-functional or poly-functional linker group MULTICON comprises:

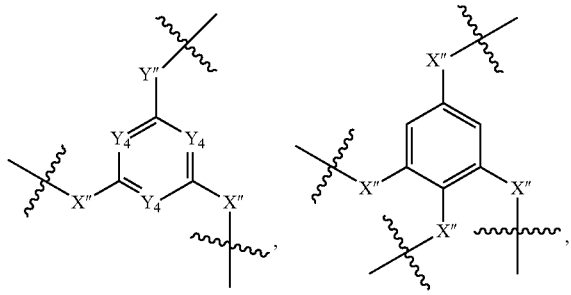

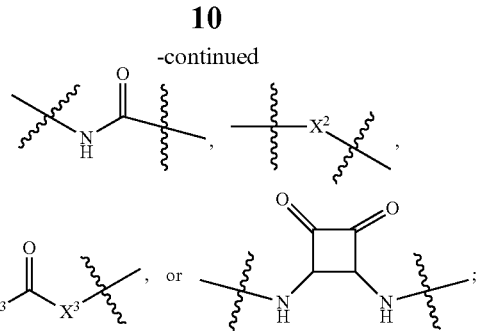

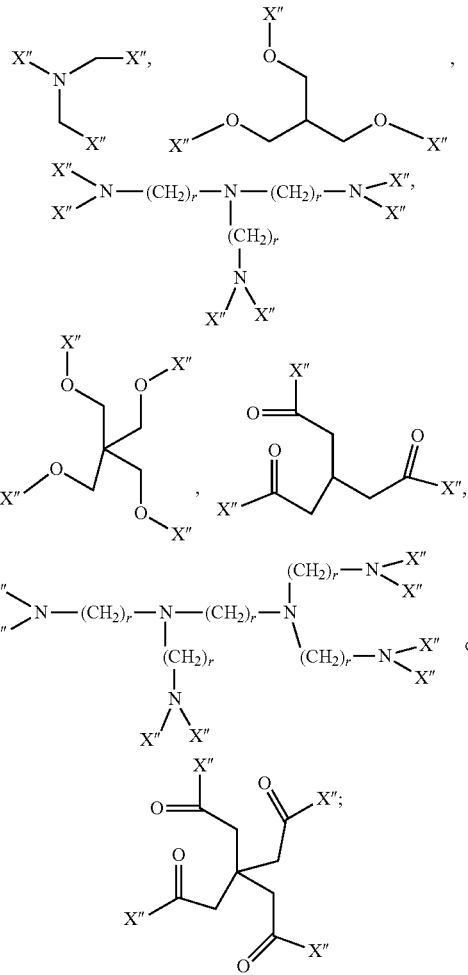

Wherein X2 is O, S, NR4, S(O), S(O)2, —S(O)2O, —OS(O)2 or OS(O)2O; X3 is O, S, NR4; R4 is a H, C1-C3 alkyl or alkanol group, or a —C(O)(C1-C3) group; or a pharmaceutically acceptable salt form thereof.

In one embodiment of the present invention, the linker L1 and/or L2 are/is

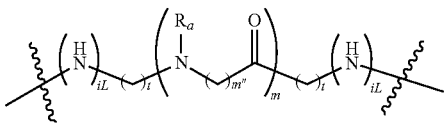

group; wherein Ra is H or CH3; m is an integer from 1 to 12; m" is an integer of 1, 2, 3, 4, 5 or 6; t is 0, 1, 2, 3, 4, 5 or 6; and iL is 0 or 1.

In one embodiment of the present invention, the linker L1 and/or L2 are/is

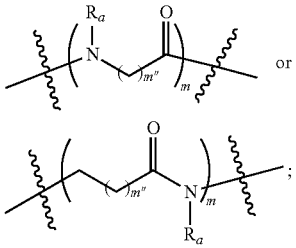

wherein Ra is H; m" is an integer of 1, 2, 3, 4, 5 or 6, and m is 1, 2, 3, 4, 5 6, 7, 8, 9, 10, 11 or 12.

In one embodiment of the present invention, L1 and/or L2 in the compound is a polyethylene glycol linkage having a length of from 1 to 12 diol units, or extending through the CON group to a second polyethylene a polyethylene glycol linkage of a diol linkage; the polyethylene glycol linkage has a length of from 1 to 12 diol units and the second polyethylene glycol linkage is from 1 to 12 diols in length unit.

In one embodiment of the present invention, the CON group is

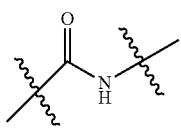 [SMILES: *NC(*)=O]

or

Wherein Y4 is CH or N; and each X" is independently derived from an electrophilic or nucleophilic group, which is not limited to (CH2)n"O, (CH2)n"NRCON, (CH2)n" S, (CH2)n", (CH2)n"C═O or a CON group; the substituent RCON is H or a C1-C3 alkyl group, especially H or CH3, and n" is 0, 1, 2 or 3; r is an integer from 1 to 12; and if present, the CON group is

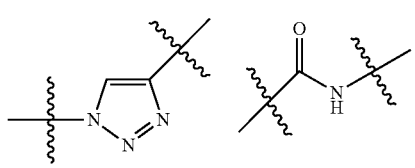

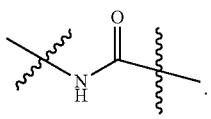 [SMILES: *NC(*)=O]

In one embodiment of the present invention, A has a moiety of the formula:

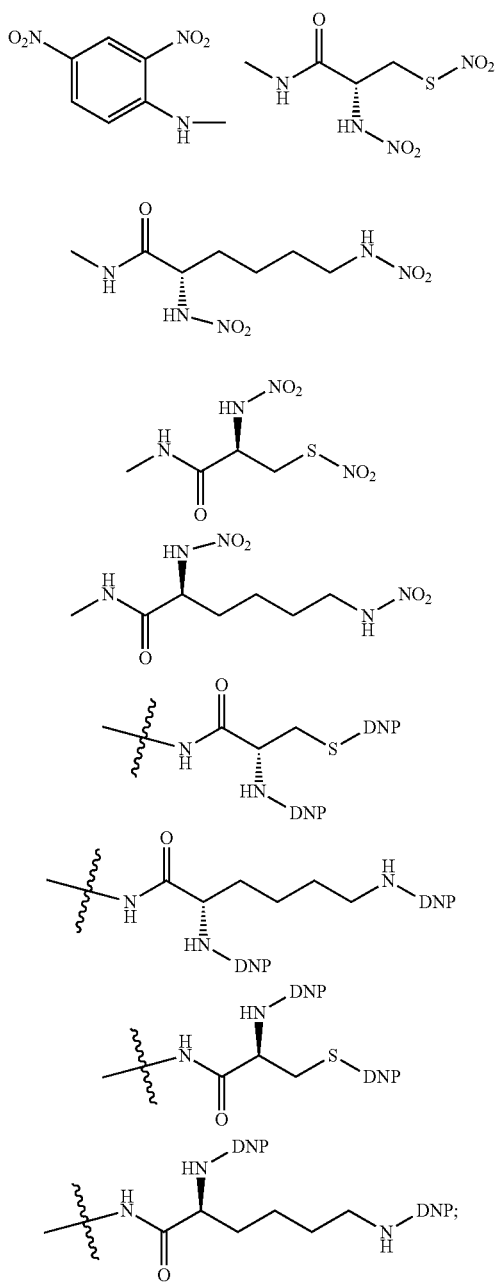

Wherein the DNP group optionally links with the amino acid moiety through an X group; X is O, CH2, NR1, SO, SO2, —S(O)2O, —OS(O)2 or —OS(O)2O.

In one embodiment of the present invention, A has a moiety of the formula:

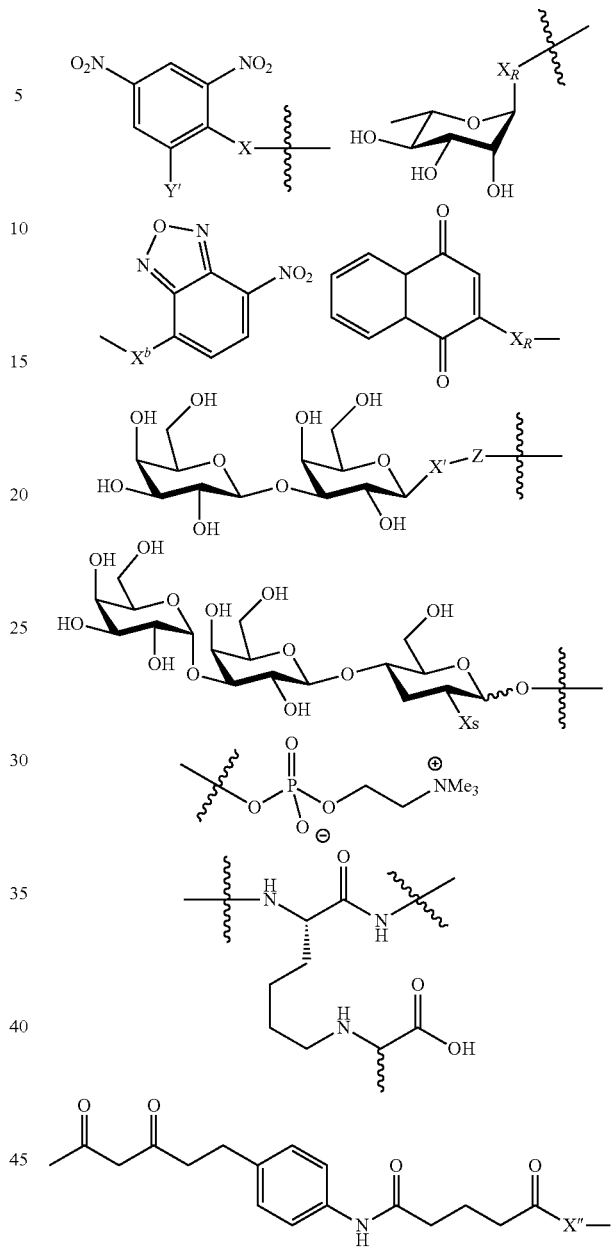

Wherein Y' is H or NO2; X is O, CH2, NR1, SO, SO2, —S(O)2O, —OS(O)2 or —OS(O)2O; R1 is H, C1-C3 alkyl or —C(O)(C1-C3) group; Xs is OH or NHAc; XR is O or S; Xb is a chemical bond O, CH2, NR1 or S; X is CH2, O, N—R' (R1' is H or C1-C3 alkyl) or S; X" is O, CH2, NR1 (R1 is H, C1-C3 alkyl or —C(O)(C1-C3) group) Z is a chemical bond, monosaccharide, disaccharide, oligosaccharide, glycoprotein or glycolipid.

The Advantages of this Invention (1) The antibody-recruitment domains used in the present invention are all conventional small molecules or easily obtained ZZ domain, both of them can recruit related antibodies from human serum in high efficiency.

(2) The cell-binding domains used in the present invention are all readily synthesized polypeptides, cyclic peptides or antibody proteins which are easily obtained by fermentation, and all of them have the high affinity to antigens over-expressed on cell surface, and their binding ability are no less than traditional monoclonal antibodies.

(3) In the present invention, the conjugation strategies is not complicated, and the product is also easy to be purified. For example, the reactions could be performed in a physiological environment by using Sortase A or click chemistry.

(4) The bi-functional molecules provided by the present invention can specifically binding tumor cell cells, and the semi-binding constant is usually less than 10 nM; and they also can effectively recruit anti-DNP, anti-Rha and other antibodies on tumor surface, resulting in the inducement of CDC or ADCC to kill tumor cells (20%-90%). The present invention also evaluate the effect of linkers (including different lengths, kinds) between the cell-binding domains and antibody-recruitment domains on tumor killing efficacy, which can provide valuable foundation and reference for the development of similar tumor drugs in the future.

DESCRIPTION OF PREFERRED EMBODIMENTS

The following embodiments are used to describe the present presentation. However, they are not intended to limit the scope of the present invention.

Embodiment 1

In this embodiment, the anti-EGFR nanobody 7D12 and two small molecules (GGG-triEGDNP, GGG-hexEGDNP) were utilized.

1. The Synthesis of Small Molecules GGG-triEGDNP and GGG-hexEGDNP.

The synthesis procedures are as follows.

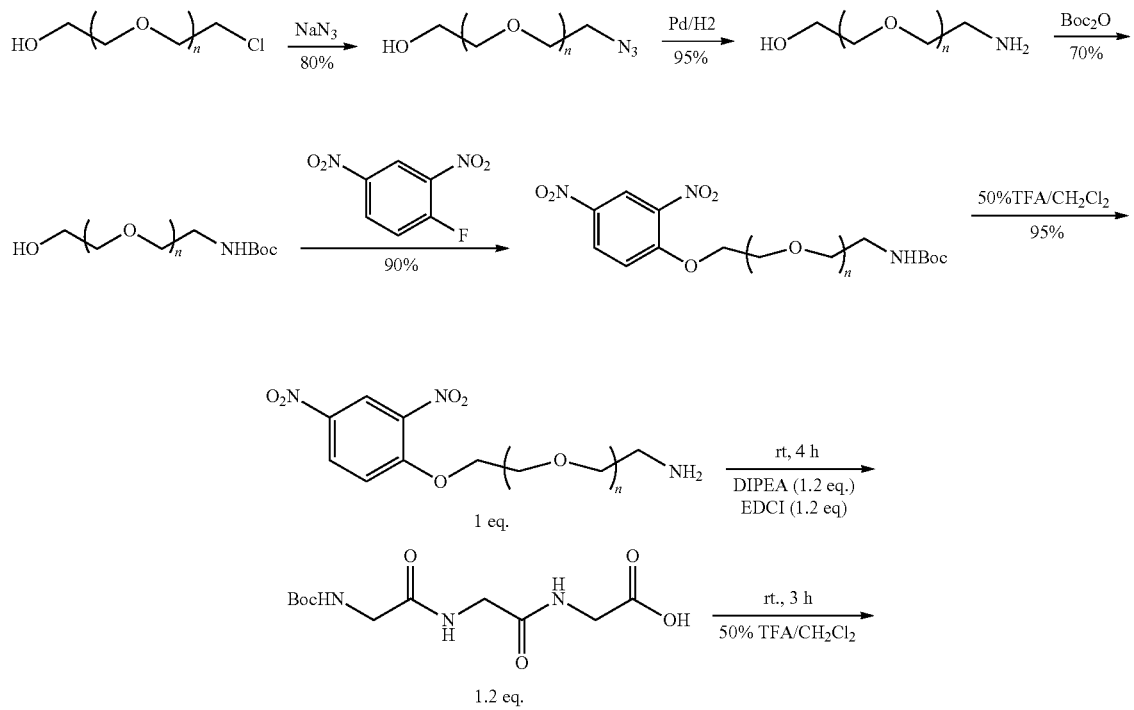

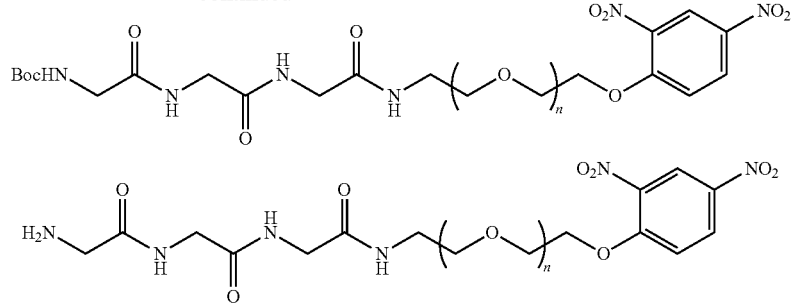

Figure 1:
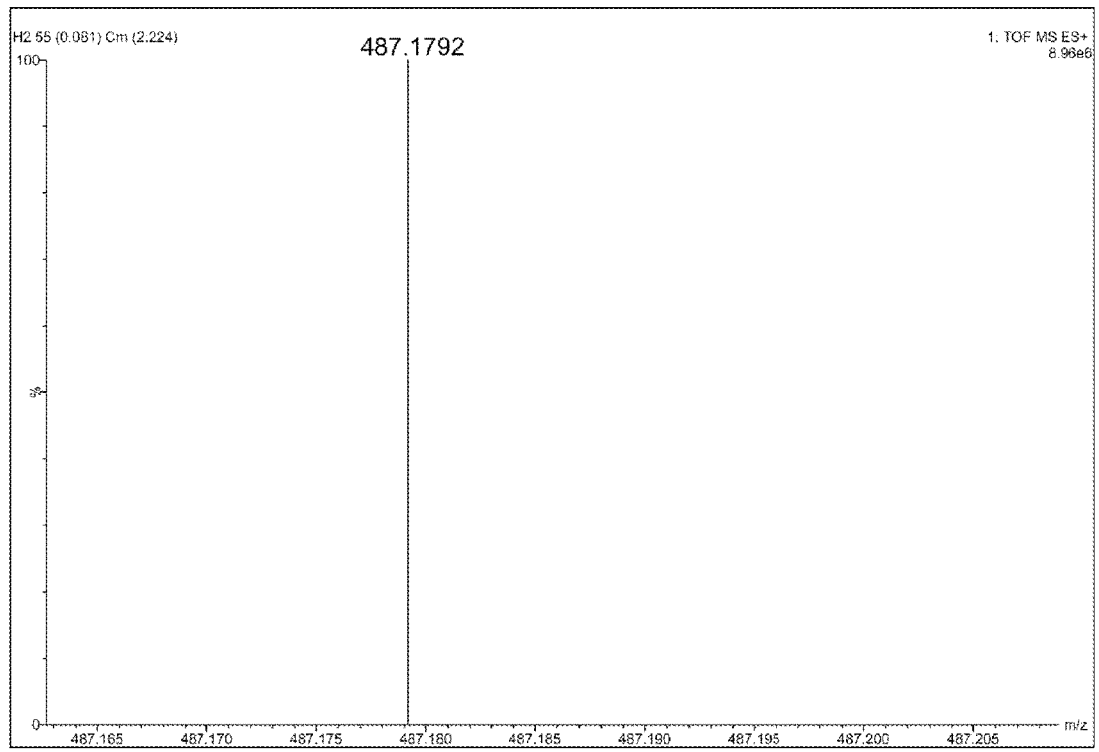
FIG. 1 provides the TOF-MS of GGG-triEGDNP (A) and GGG-hexEGDNP (B).
Figure 1:
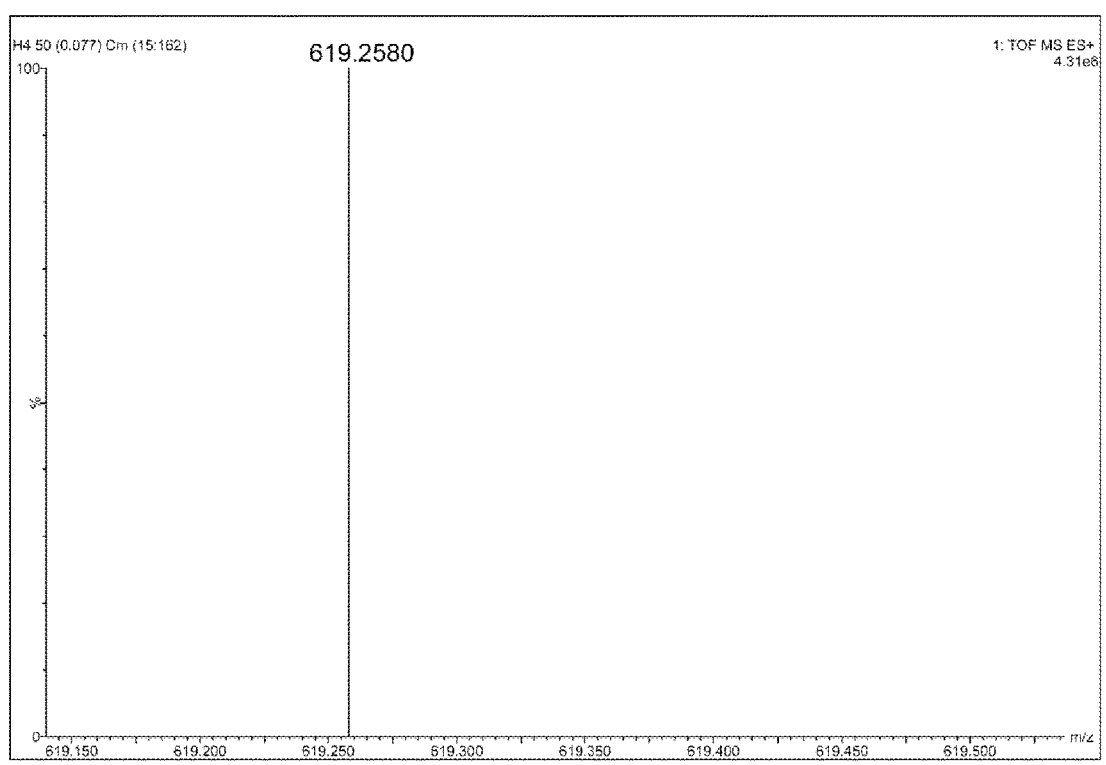

As shown in FIG. 1, the observed molecular weight of GGG-triEGDNP and GGG-hexEGDNP are 487.1792 (M+H+) and 619.2520 (M+H+), respectively, both of which are in line with the calculated molecular weight.

2. The Expression of Anti-EGFR Nanobody 7D12.

The amino sequence of 7D12 are as follows (related NCBI sequence ID: 4KRL_B):

```
                                          (SEQ ID NO: 1)
maqvkleesgggsvqtggslrltcaasgrtsrsygmgwfrqapgkerefv sgiswrgdstgyadsvkgrftisrdnakntvdlqmnslkpedtaiyycaa aagsawygtlyeydywgqgtqvtvssaaaeqkliseedlngaalpetggh hhhhh
```

Fermentation procedures: the gene fragment of 7D12 was firstly inserted into commercial expression plasmid pET28a to obtain pET28a-7D12. Then the engineered plasmid was transformed into *E. coli* BL21(DE3). The positive clone was subsequently cultivated in LB medium containing 0.1% kanamycin overnight at 37° C. Next, the described medium was diluted (1-10%) with TB medium and incubated at 37° C. When the OD600 reached 0.6-1.2, IPTG was added to a final concentration of 0.1-1.0 mM and the induction was performed for 24 h at 16-30° C. The cells were then harvested using centrifugation and resuspended in PBS buffer. The cells were then disrupted by ultrasonication. With another centrifugation step, the supernatant was collected for further protein purification and desalting. After purification and desalting, 7D12 was confirmed by SDS-PAGE. The result of SDS-PAGE showed one band with molecular weight at 16.7 KD.

3. The Synthesis of 7D12-triEGDNP and 7D12-hexEGDNP.

The reaction was performed in Tris-HCl buffer at 4-37° C. for 10-120 min using enhanced SrtA. The unreacted 7D12 and enhanced SrtA were removed using Ni2+ coated magnetic beads and the excess small molecules were removed using dialysis or gel column. The purified 7D12-triEGDNP and 7D12-hexEGDNP were finally collected using sterile filtration and kept at −20° C. for further use.

4. In Vitro Evaluation (1) Cell Culture

A431 (EGFR positive) and MCF7 cells (EGFR negative) were grown in DMEM supplemented with 10% FBS, 1% penicillin-streptomycin. 4T1 cells (murine EGFR positive) were grown in RPMI supplemented with 10% FBS, 1% penicillin-streptomycin. All cells were cultured at 37° C. in a 5% CO2 humidified atmosphere.

(2) Flow Cytometry Assay

① Cells were cultured and detached with trypsin-EDTA and then resuspended to 1.0×105 cells/mL. Forty thousand of these cells were added into tubes. ② Nanobody 7D12 and DNP conjugated 7D12 were then added to a final concentration of 250 nM, followed which Alexa 488-conjugated rabbit anti-DNP IgG antibodies were added. In the negative control group, cells were treated with PBS instead of nanobody. These cells were incubated on ice for 60 min, ③ washed with flow cytometry buffer and then analyzed using an Accuri C6 flow cytometer.

Figure 2:
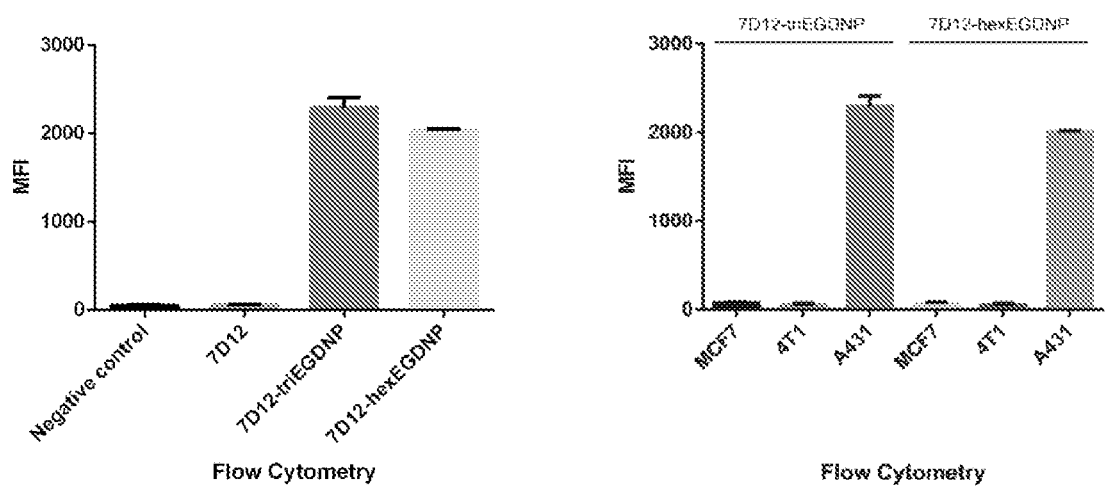
FIG. 2 provides the flow cytometry of cells treated with PBS (negative control), 7D12, 7D12-triEGDNP and 7D12-hexEGDNP (left picture); and the flow cytometry of different cell lines treated with DNP conjugated 7D12 (right picture). MFI: mean fluorescence intensity.

As shown in FIG. 2, cells treated with 7D12 have no fluorescence intensity increase compared to negative control, indicating that 7D12 could not accumulate anti-DNP IgGs on target cells. Additionally, the significant fluorescence intensity increase were observed A431 cells treated with DNP conjugated 7D1, but not that of MCF7 neither 4T1 cells, indicating that the DNP conjugated could specifically bind to human EGFR positive cells, but not EGFR negative neither murine EGFR positive cells.

(3) ADCC Assay

① A431 cells were seeded in 96-well plates at a concentration of 10,000 cells/well and then treated with 7D12 and DNP conjugated 7D12 in the presence of rabbit anti-DNP IgG antibodies. ② Next, freshly isolated human peripheral blood mononuclear cells were added to each well. ③ Following the incubation period, the supernatant was transferred onto a new black 96-well and detected using LDH kit.

Figure 3:
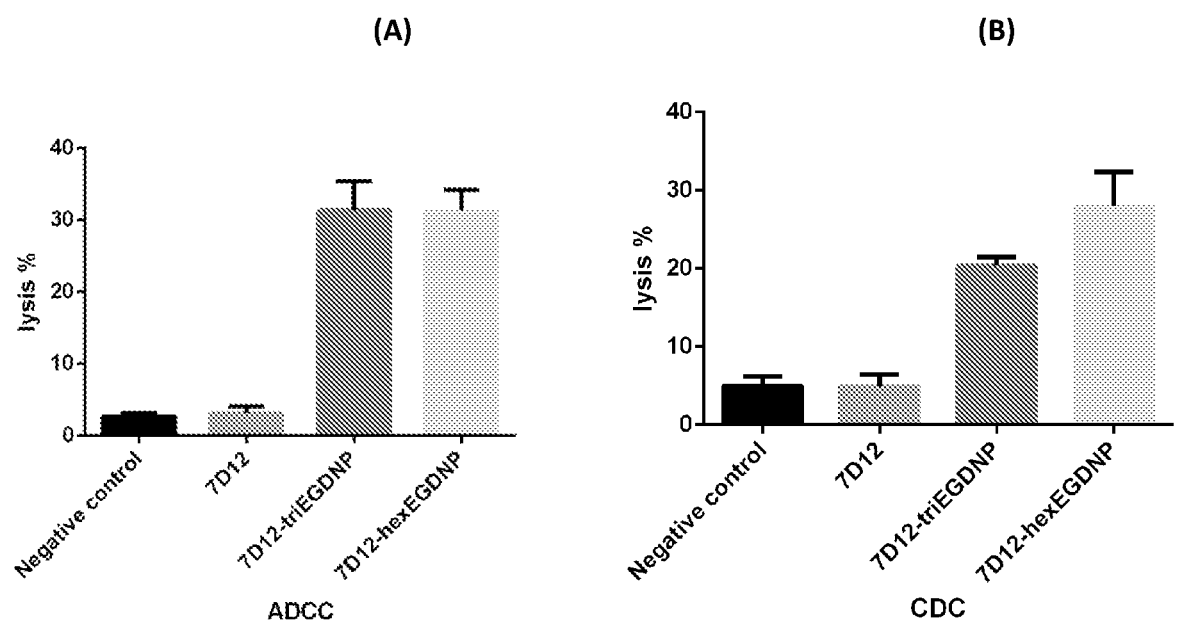
FIG. 3 provides the in vitro cytotoxicity of 7D12, 7D12-triEGDNP and 7D12-hexEGDNP. (A) ADCC. (B) CDC.

The results were shown in FIG. 3(A), the ADCC efficacy of 7D12-triEGDNP and 7D12-hexEGDNP could reach 31% and 37%, respectively. They were both significantly higher than that of cells treated with 7D12 (Approximated 5%), indicating that both 7D12-triEGDNP and 7D12-hexEGDNP could induce ADCC, and there was no significant difference between 7D12-triEGDNP and 7D12-hexEGDNP was observed.

(4) CDC Assay

① DA431 cells were seeded in 96-well plates at a concentration of 5000 cells/well and then treated with 7D12 and DNP conjugated 7D12 in the presence of rabbit anti-DNP IgG antibodies. ② Next, diluted rabbit complement were added to each well. ③ Following the incubation period, the results detected using cck8 kit.

The results were shown in FIG. 3(B), the CDC efficacy of 7D12-triEGDNP and 7D12-hexEGDNP could reach 21% and 27%, respectively. They were both significantly higher than that of cells treated with 7D12 (Approximated 5%), indicating that both 7D12-triEGDNP and 7D12-hexEGDNP could induce CDC, and the CDC induced by 7D12-hexEGDNP was slightly stronger than that of 7D12-triEGDNP.

Embodiment 2

In this embodiment, the anti-HER2 nanobody and two small molecules (GGG-triEGRha, GGG-hexEGRha) were utilized.

The synthesis of small molecules GGG-triEGRha and GGG-hexEGRha.

The synthesis procedures are as follows.

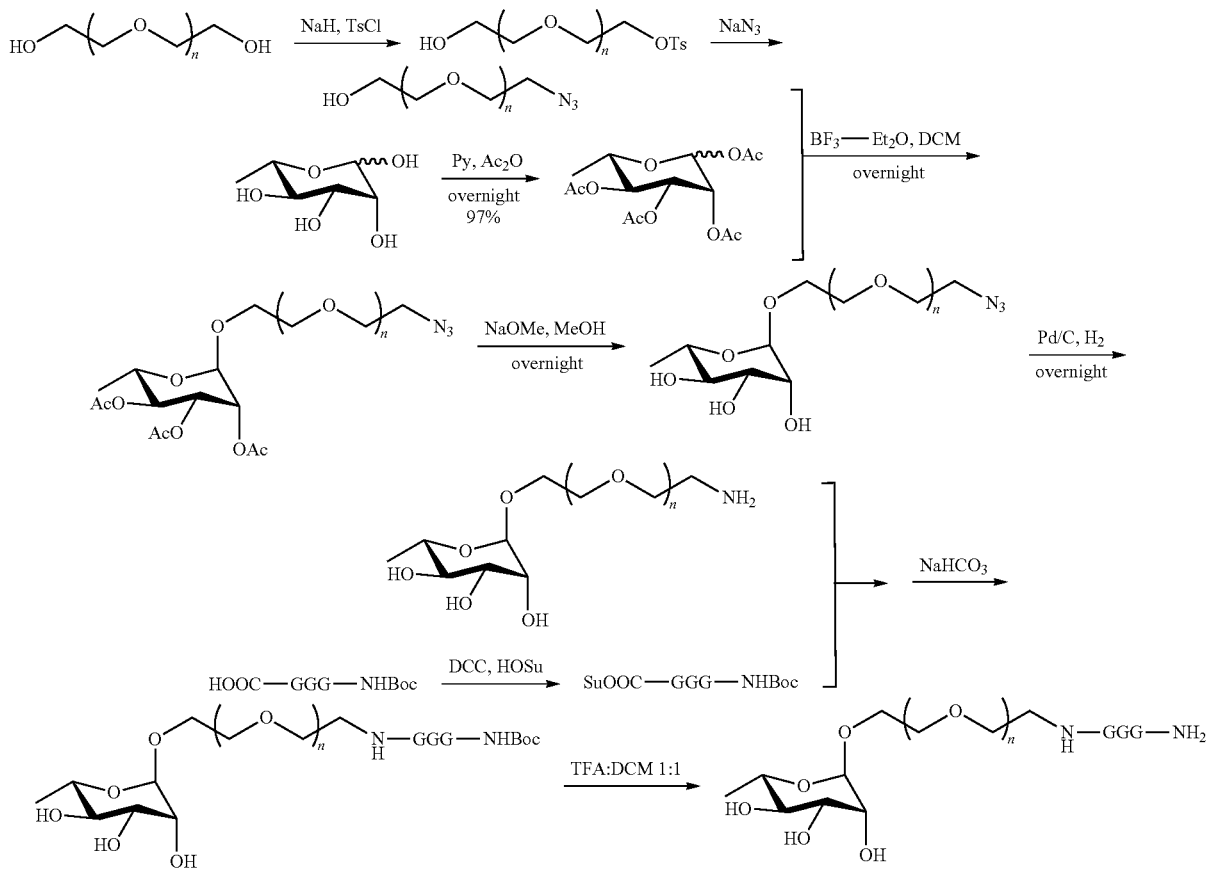

Figure 4:
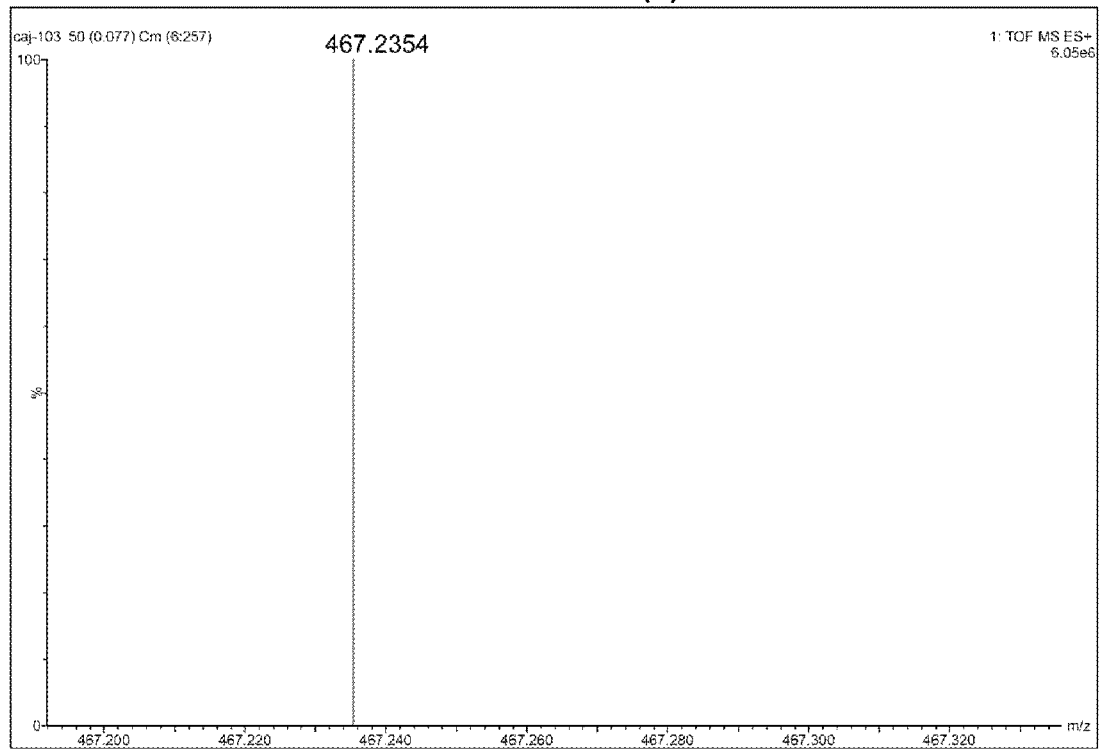
FIG. 4 provides the TOF-MS of GGG-triEGRha (A) and GGG-hexEGRha (B).
Figure 4:
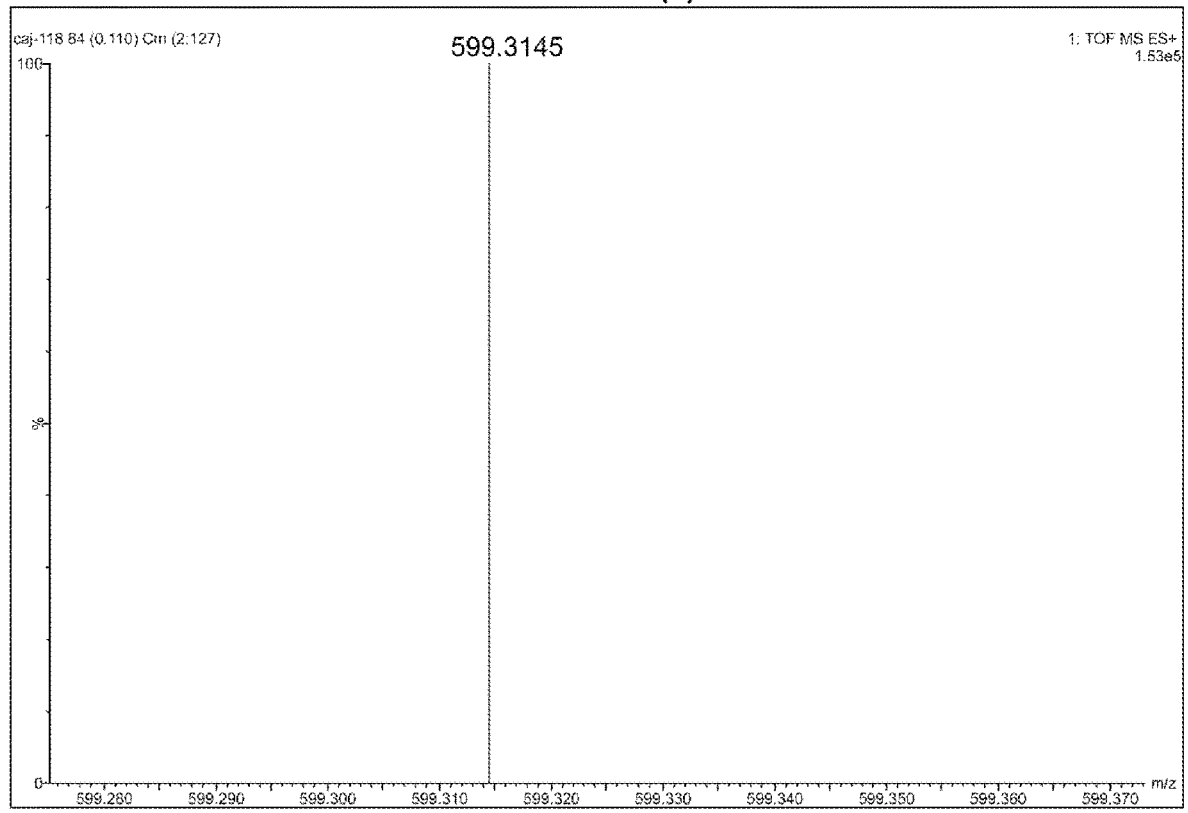

As shown in FIG. 4, the observed molecular weight of GGG-triEGRha and GGG-hexEGRha are 467.2354 (M+H+) and 599.3145 (M+H+), respectively, both of which are in line with the calculated molecular weight.

2. The Expression of Anti-EGFR Nanobody C7b

The amino sequence of C7b are as follows (related NCBI sequence ID: AFN61318.1):

```
                                            (SEQ ID NO: 2)
mqvqlvqsggglvqaggslrlscaasgrtfssyamawfrqapgkerefva aiswsganiyvadsvkgrftisrdnakdtvylqmnslkpedtavyycavk lgfapveerqydywgqgtqvtvsslpetgg
```

Fermentation procedures: the gene fragment of C7b was firstly inserted into commercial expression plasmid pET22b to obtain pET22b-C7b. Then the engineered plasmid was transformed into E. coli BL21(DE3). The positive clone was subsequently cultivated in LB medium containing 0.1% ampicillin overnight at 37° C. Next, the described medium was diluted (1-10%) with TB medium and incubated at 37° C. When the OD600 reached 0.6-1.0, IPTG was added to a final concentration of 0.1-1.0 mM and the induction was performed for 24 h at 16-30° C. The cells were then harvested using centrifugation and resuspended in PBS buffer. The cells were then disrupted by ultrasonication. With another centrifugation step, the supernatant was collected for further protein purification and desalting.

3. The Synthesis of C7b-triEGRha and C7b-hexEGRha

The reaction was performed in Tris-HCl buffer at 4-37° C. for 10-120 min using enhanced SrtA. The unreacted C7b and enhanced SrtA were removed using Ni2+ coated magnetic beads and the excess small molecules were removed using dialysis or gel column. The purified C7b-triEGRha and C7b-hexEGRha were finally collected using sterile filtration and kept at −20° C. for further use.

4. In Vitro Evaluation (1) Cell Culture

SKBR3 (HER2 positive) and MCF7 cells (HER2 negative) were grown in DMEM supplemented with 10% FBS, 1% penicillin-streptomycin. All cells were cultured at 37° C. in a 5% CO2 humidified atmosphere.

(2) Flow Cytometry Assay

① Cells were cultured and detached with trypsin-EDTA and then resuspended to 1.0×105 cells/mL. Forty thousand of these cells were added into tubes. ② Nanobody C7b and Rha conjugated C7b were then added to a final concentration of 250 nM, followed which Alexa 488-conjugated rabbit anti-Rha IgG antibodies were added. In the negative control group, cells were treated with PBS instead of nanobody.

These cells were incubated on ice for 60 min, ③ washed with flow cytometry buffer and then analyzed using an Accuri C6 flow cytometer.

Figure 5:
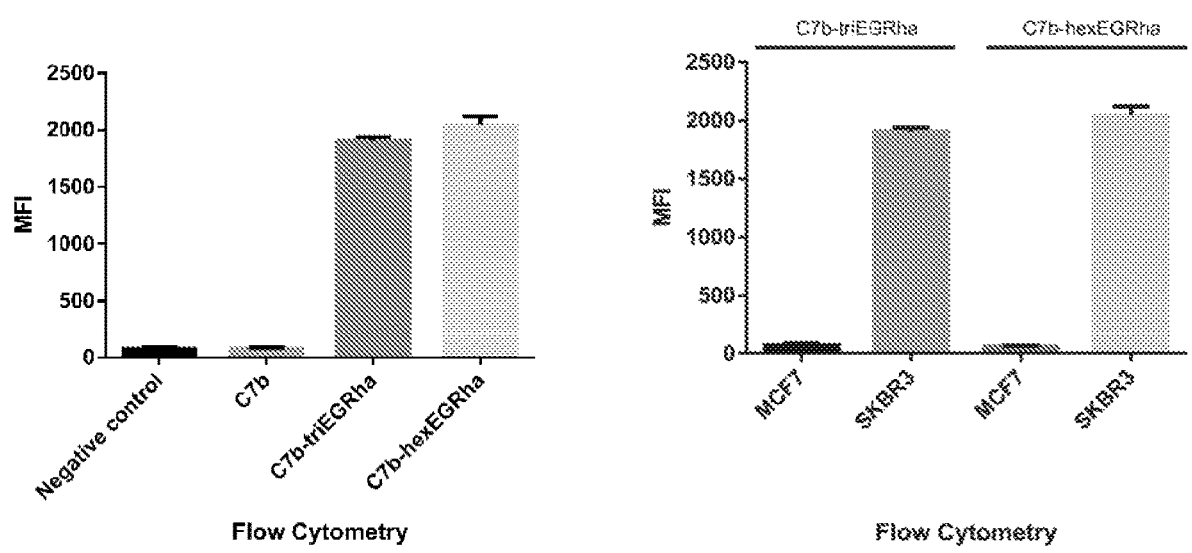
FIG. 5 provides the flow cytometry of cells treated with PBS (negative control), C7b, C7b-triEGRha and C7b-hexEGRha (left picture); and the flow cytometry of different cell lines treated with Rha conjugated C7b (right picture). MFI: mean fluorescence intensity.

As shown in FIG. 5, cells treated with C7b have no fluorescence intensity increase compared to negative control, indicating that C7b could not accumulate anti-Rha IgGs on target cells. Additionally, the significant fluorescence intensity increase were observed SKBR3 cells treated with Rha conjugated C7b, but not that of MCF7, indicating that the Rha conjugated could specifically bind to HER2 positive cells, but not HER2 negative cells.

(3) ADCC Assay

① SKBR3 cells were seeded in 96-well plates at a concentration of 10,000 cells/well and then treated with C7b and Rha conjugated C7b in the presence of rabbit anti-Rha IgG antibodies. ② Next, freshly isolated human peripheral blood mononuclear cells were added to each well. ③ Following the incubation period, the supernatant was transferred onto a new black 96-well and detected using LDH kit.

Figure 6:
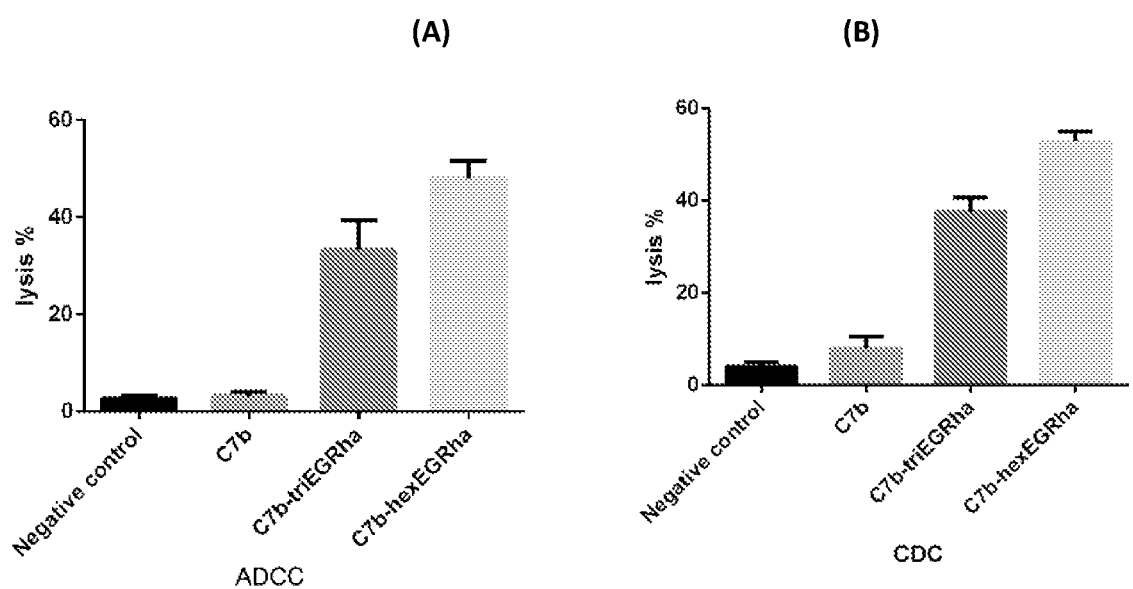
FIG. 6 provides the in vitro cytotoxicity of PBS (negative control), C7b, C7b-triEGRha and C7b-hexEGRha. (A) ADCC. (B)CDC.

The results were shown in FIG. 6(A), the ADCC efficacy of C7b-triEGRha and C7b-hexEGRha could reach 32% and 43%, respectively, indicating that both C7b-triEGRha and C7b-hexEGRha could induce ADCC, and C7b-hexEGRha has higher ADCC efficacy than that of C7b-triEGRha.

(4) CDC Assay

① SKBR3 cells were seeded in 96-well plates at a concentration of 5000 cells/well and ② then treated with C7b and Rhaconjugated C7b in the presence of 20% normal human serum (the source of anti-Rha IgG and complement). ③ Following the incubation period, the results detected using cck8 kit.

The results were shown in FIG. 6(B), the CDC efficacy of C7b-triEGRha and C7b-hexEGRha could reach 36% and 47%, respectively, indicating that both C7b-triEGRha and C7b-hexEGRha could induce CDC, and C7b-hexEGRha has higher CDC efficacy than that of C7b-triEGRha.

Embodiment 3

Rhamnose (Rha) was coupled to the LHRH peptides and targeted to kill tumor cells by recruiting antibodies existing in the body to mediate immune effects.

The embodiments of the synthesis of LHRH-Rhamnose conjugate (LHRH-Rhamnose, LHRH-Rha) are:

Based on the study of structure-activity relationship of LHRH, [6-D-Lys(N3)]-LHRH peptides came from that the substitution of D-lysine (D-Lys(N3)) with azide group (—N3) was carried out at the position of 6-glycine without affecting its activity. (The amino acid sequence of [6-D-Lys(N3)]-LHRH is as follows: pyroglutamate-histidine-tryptophan-serine-tyrosine-D-lysine(-N3)-leucine-arginine-valine-glycine-amino group, Glp-His-Trp-Ser-Tyr-D-Lys(N3)-Leu-Arg-Pro-Gly-NH2 (SEQ ID NO:3). Wherein Glp is pyroglutamic acid.

[6-D-Lys(N3)]-LHRH peptides were synthesized by solid-phase peptide synthesis using Fmoc protecting group strategy. according to the sequence of Glp-His-Trp-Ser-Tyr-D-Lys(N3)-Leu-Arg-Pro-Gly-NH2 (SEQ ID NO:3) (Glp is pyroglutamic acid and no Fmoc protection), using TBTU as a condensing agent, from the C-terminus Gly to the N-terminal Glp gradual condensation. After sequence synthesis, the polypeptide was cleaved from the resin by the addition of a cleavage reagent (TFA:Tis:H2O=95:2.5:2.5). The crude peptide was obtained by precipitation with ice diethyl ether, and then purified by HPLC to obtain the peptide [D-Lys6]-LHRH, which was confirmed by mass spectrometry, and [M+Na+] was 1301.6, which was the correct product.

Wherein, the synthesis of the azide-containing D-lysine is (mass data [M+Na+] 417.1, which was the correct compound):

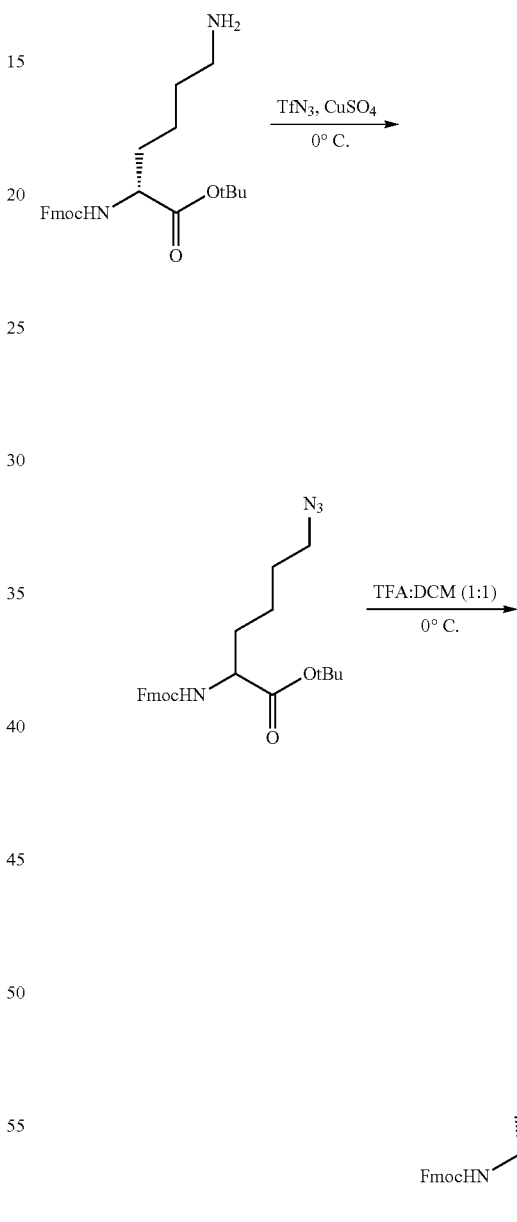

The embodiment of synthesizing a rhamnose (Rha) derivative is as follows: Rha molecules were assembled by oligo-glycol (option n=0, 2, 5) tethers, and the other end of the tether was an alkynyl group coupled with the above LHRH polypeptide derivative (SEQ ID NO:3) by a click reaction, the synthesized compound is Glp—His—Trp—Ser—Tyr—D—Lys—Leu—Arg—Pro—Gly—NH2

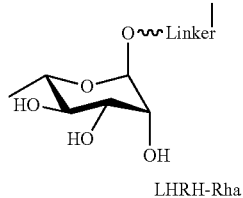

LHRH-Rha , the synthetic route is as follows:

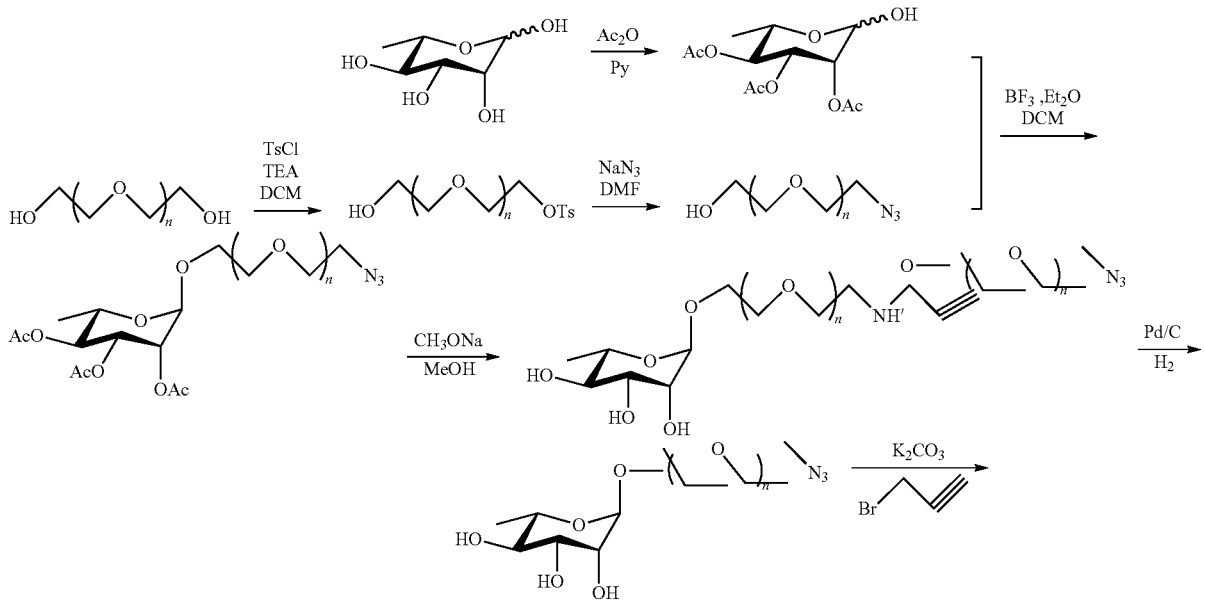

Under the conditions catalyzed by copper sulfate and sodium ascorbate, the Rha derivative and the LHRH derivative were linked by a click reaction to obtain a LHRH-Rha coupling product, and the mass spectrometry confirmed the coupling. The linker is oligo-glycol (n=0, 2, 5), respectively represented as LHRH-Rha (mass molecular weight [M+Na+] was 1560.7), LHRH-TEG-Rha (mass spectrometry molecular weight [M+Na+] was 1648.8), LHRH-HEG-Rha (mass molecular weight [M+Na+] was 1780.9).

The Embodiment of Cell Experiments:

Cell Culture:

Commercialized MCF7 cells (LHRH-R positive) and UCI-107(LHRH-R negative) were grown in DMEM supplemented with 10% FBS, 1% penicillin-streptomycin. All cells were cultured at 37° C. in a 5% CO2 humidified atmosphere.

Flow Cytometry Assay:

① Cells were cultured and detached with trypsin-EDTA and then resuspended to 1.0×105 cells/mL. Forty thousand of these cells were added into sterile centrifuge tubes. ② LHRH, LHRH-Rha, LHRH-TEG-Rha and LHRH-HEG-Rha compounds were added at a final concentration of 250 nM. For the blank group (Negative), the corresponding volume of PBS was added. And anti-Rha antibody at a final concentration of 20 μg/mL in all groups. These cells were incubated on ice for 60 min, washed with flow cytometry buffer. And fluorescent secondary antibody was immediately added in all groups. These cells were incubated on ice for 30 min, ③ washed with flow cytometry buffer and then analyzed using an Accuri C6 flow cytometer.

The embodiment of ADCC experiments:

① MCF7 or UCI-107 cells were seeded in 96-well plates at a concentration of 10,000 cells/well and then treated with LHRH, LHRH-Rha, LHRH-TEG-Rha and LHRH-HEG-Rha at a final concentration of 250 nM and a certain concentration of anti-Rha antibody. ② Following the incubation period, freshly extracted PBMC cells were added at a certain effective target ratio, ③ and the supernatant was treated by centrifugation for minutes, using LDH method to measure the cytotoxicity.

The embodiment of CDC experiments:

① MCF7 cells or UCI-107 were seeded in 96-well plates at a concentration of 5000 cells/well and then treated with LHRH, LHRH-Rha, LHRH-TEG-Rha and LHRH-HEG-Rha at a final concentration of 250 nM and a certain concentration of anti-Rha antibody. Following the incubation at 37° C. for 2 h, next, diluted rabbit complement at a final concentration of 10% were added to each well. Following the incubation at 37° C. for 1 h, the results detected using cck8 kit.

Figure 7:
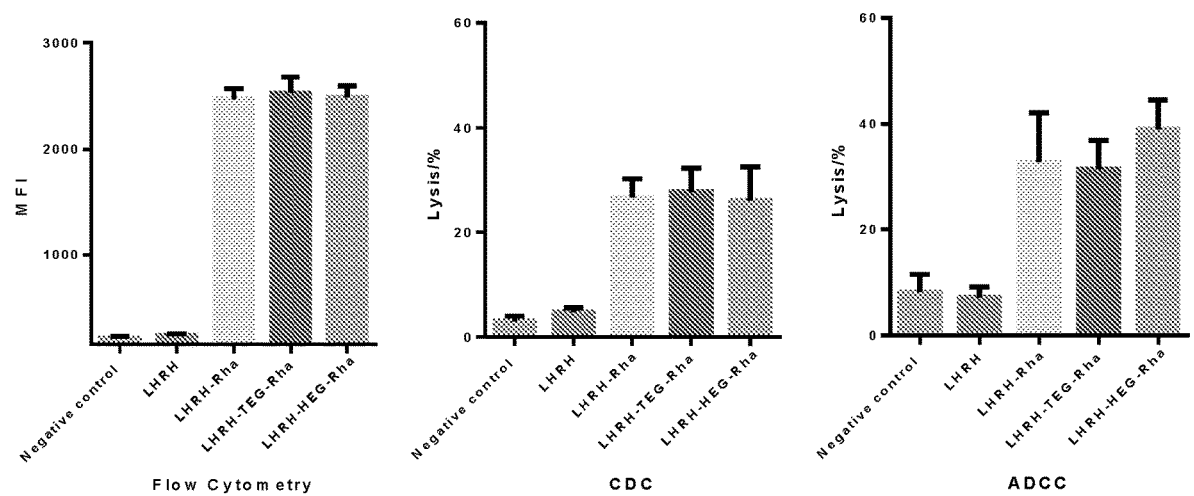
FIG. 7 provides the flow cytometry (left picture), CDC (middle picture) and ADCC (right picture) assays of MCF7 cells treated with PBS (negative control), LHRH peptide, LHRH-Rha, LHRH-TEG-Rha or LHRH-HEG-Rha. MFI: mean fluorescence intensity.

The results of flow cytometry, ADCC and CDC were shown in FIG. 7. LHRH-Rha, LHRH-TEG-Rha and LHRH-HEG-Rha conjugated compounds could recruit anti-Rha antibodies and target high expression of LHRH MCF-7 tumor cells, and mediate the immune response CDC and ADCC to further kill MCF-7 tumor cells, and these three compounds were mediated by the same immune killing effect (CDC-mediated killing rate was about 26%, ADCC-mediated killing rate was about 33%. In the present embodiment, the length of the linking arm had little effect on the activity.

Embodiment 4

NGR peptide is the peptide containing the sequence of Asparagine-Arginine-Glycine. The linear peptide has CYG-GRGNG (SEQ ID NO:4), CNGRCVSGCAGRC (SEQ ID NO:5), GNGRGGVRSSSRTPSDKYC (SEQ ID NO:6), etc. NRG peptide is a targeting peptide that can bind CD13 receptor on tumor neovascularization endothelial cells and can effectively target tumor cells. Therefore, this invention designs and synthesizes an NGR-based antibody recruitment bifunctional molecule. The structure of DNP was coupled to NGR. By recruiting anti-DNP antibodies and targeting tumor neovascularization endothelial cells with high CD13 expression, the immune response can be mediated to target and kill tumor cells.

The synthesis of NGR-DNP conjugates is implemented as follows:

of impurities, pass through the silica gel column. The product was 0.26 g in 80% yield.

Synthesis of compound 4: First synthesized the peptide chain GGGCNGRC (SEQ ID NO:7) (G, C, N, R represent amino acid glycine, cysteine, asparagine, arginine respectively). The Fmoc-Cys (Acm)-Wang resin (0.1 mmol) resin was swelled overnight in a solid phase synthesis tube as a solid phase carrier. Add 20% piperidine/DMF solution (5 ml) and shake it in a shaker for 15 min to remove Fmoc group. Then Fmoc-Arg-OH (0.25 mmol), HBTU (0.25 mmol), Dipea (0.5 mmol) was dissolved in 5 ml of DMF solution, added to the resin and shaken in a shaker for 2 h. The reaction was monitored by ninhydrin solution. The Fmoc protecting group was again removed and the above procedure was repeated until the peptide chain was synthesized.

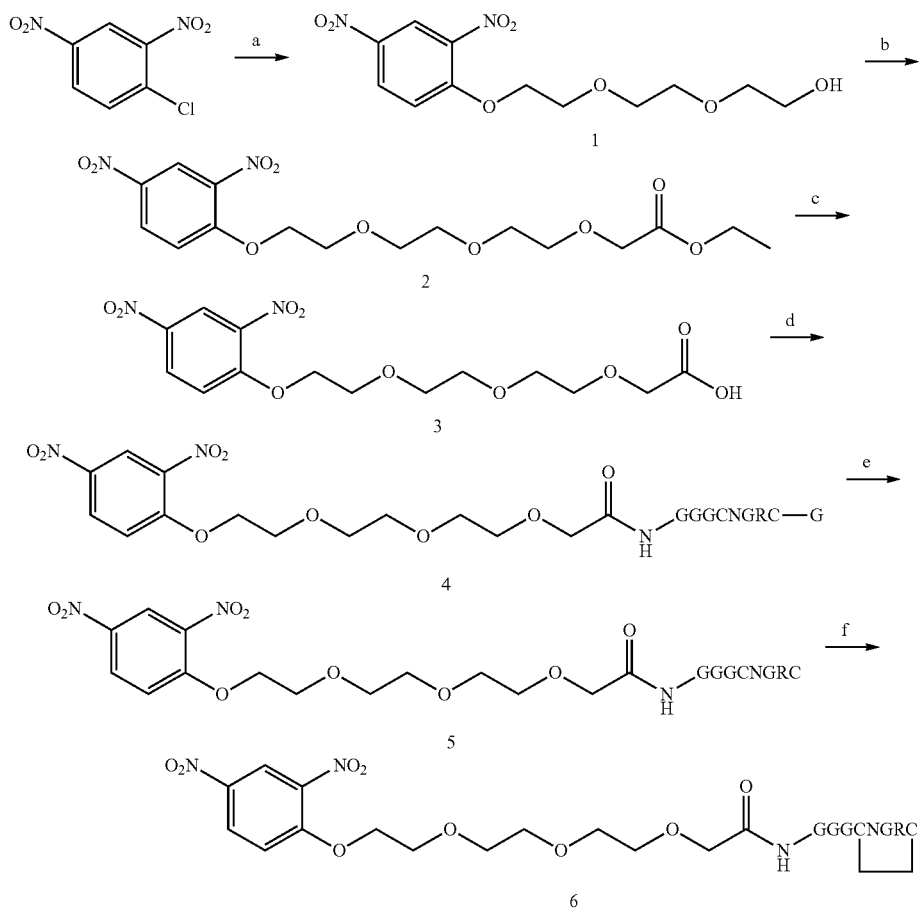

Figure 8:
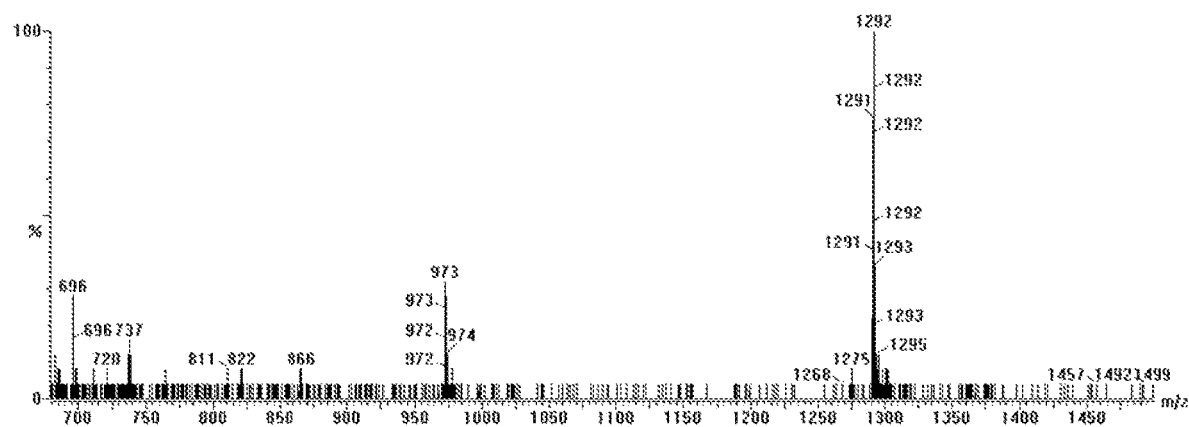
FIG. 8 provides the MS of molecule NGR-DNP.

Synthesis of compound 3 (DNP-TEG-COOH): 0.35 g of compound 2 (DNP-TEG-COOEt) was dissolved in 1:1 THF/H2O solution (15 ml/15 ml) at 0° C., then 0.4 g of potassium carbonate was added into the solution for overnight reaction. After the reaction, the THF was evaporated and the solution was extracted with 20 ml of dichloromethane (DCM) for three times. The product was dissolved in water in a salt state. The thin layer chromatography was used to monitor the extraction of impurities in the water. The aqueous phase was neutralized with 1 mol/ml hydrochloric acid until the pH test paper became red. After evaporation, it was dissolved in DCM and filtered. If there is still a small amount Then, 0.25 mmol of Compound 3, HBTU (0.25 mmol), DIPEA (0.5 mmol) was dissolved in 5 ml of DMF solution, added to the resin, and reacted for 2 hours. Monitor the end of the reaction. Synthesis of compound 5: Compound 4 was reacted in 95% trifluoroacetic acid (TFA) solution (TFA:Tis:H2O=95:2.5:2.5) for 2 h, and the resin was cut off. Then used a large amount of ice ether to precipitate and centrifuge. The peptide was lyophilized after removing the ether and monitored by HPLC. Synthesis of compound 6: compound 5 was dissolved in acetic acid, oxidized with iodine (12) and reacted for 2-3 h. The reaction was monitored by HPLC and quenched with water after the reaction. The solution was washed few times by trichloromethane (CHCl3) to remove most iodine (12). The aqueous phase was evaporated and the crude product was purified by using a semi-preparative column. FIG. 8 shows the mass spectrometry results of the compound NGR-DNP. It can be seen that a peak with a predicted molecular weight of 973 appears, indicating that the product was successfully synthesized.

Cell assay implementation: cell culture: commercial cells HUVEC (high expression of CD13) was cultured in DMEM complete medium. All cell culture conditions were 37° C., 5% $CO_2$. Flow cytometry assay: ① The cells were digested with trypsin, resuspended in flow medium diluted to 1×105 cells. 400 μL of cells (40,000 cells) were added to a sterile EP tube. ② NGR oligopeptide (NGR peptide, amino acid sequence: GGG-cyclo-(CNGRC) (SEQ ID NO:8)) or NGR-DNP were added at a final concentration of 250 nM. In the negative control group, cells were treated with PBS. The cells were added anti-DNP (anti-DNP) antibody at a concentration of 20 μg/mL in all groups, incubate on ice for 1 h. then the cells were washed and incubated with fluorescent secondary antibody for 0.5 h. ③ The cells were thoroughly washed gently with a flow buffer, resuspended, and analyzed by instruments.

ADCC assay implementation: ① HUVEC cells were seeded in 96-well plates at a concentration of 10,000 cells/well. After the cells were fully attached, added with NGR oligopeptide (NGR peptide, amino acid sequence: GGG-cyclo-(CNGRC) (SEQ ID NO:8)) or NGR-DNP compound at a final concentration of 250 nM and immediately added a certain concentration of anti-DNP antibody. ② After incubation for a period of time, freshly extracted PBMC cells were added at a certain effect target ratio for a certain period of time. ③ The supernatant was removed by centrifugation, and cytotoxicity was measured by the LDH method.

CDC assay implementation: ① HUVEC cells were seeded in 96-well plates at a concentration of 5,000 cells/well. After the cells were fully attached, added with NGR oligopeptide (NGR peptide, amino acid sequence: GGG-cyclo-(CNGRC) (SEQ ID NO:8)) or NGR-DNP compound at a final concentration of 250 nM and added a certain concentration of anti-DNP antibody at the same time. After 2 hours of incubation at 37° C., a final concentration of 10% of the complement solution was added and incubated for 1 hour at 37° C. After the incubation, the cell viability was measured by the cck8 method.

Figure 9:
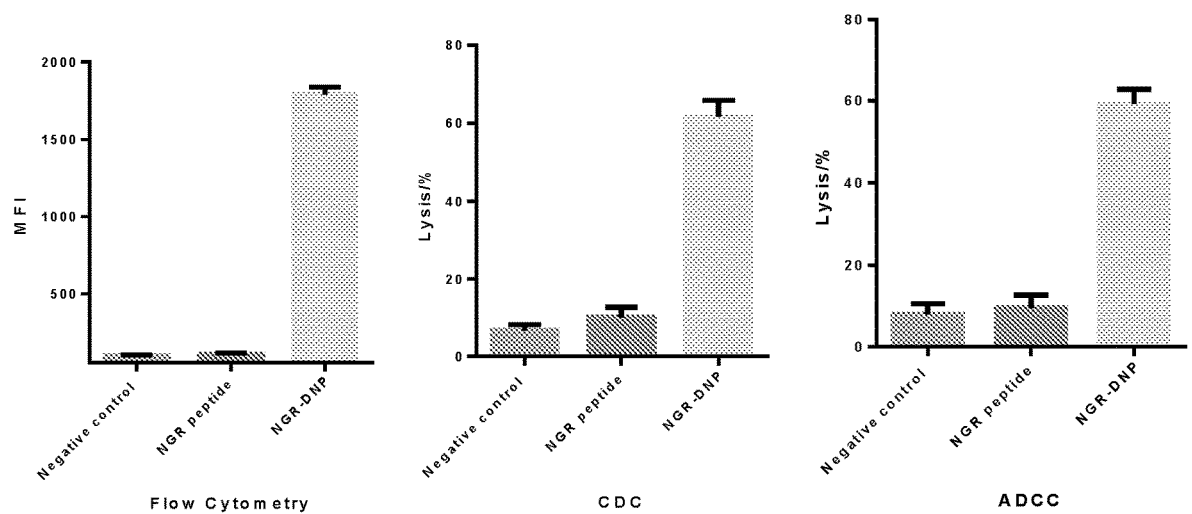
FIG. 9 provides the flow cytometry (left picture), CDC (middle picture) and ADCC (right picture) assays of MCF7 cells treated with PBS (negative control), NGR peptide or NGR-DNP. MFI: mean fluorescence intensity.

The results of flow cytometry, ADCC and CDC assay of NGR peptide (amino acid sequence: GGGCNGRC (SEQ ID NO:8)) and compound NGR-DNP are shown in FIG. 9. The experimental results indicate that NGR-DNP compounds can recruit antibodies and target tumor cells. The compounds can mediate immune responses to CDC and ADCC (cell lysis rate of approximately 60%) to further kill tumor cells.

Embodiment 5

Integrin are highly expressed on the surface of various tumor cells, but hardly expressed in normal cells, and integrin plays an important role in adhesion, migration, invasion and tumor angiogenesis of tumor cells. Therefore, integrin are an important target for cancer treatment. Arginine-glycine-aspartate (Arg-Gly-Asp, RGD) and its derivatives are used to develop tumor-targeted therapeutic strategies because as an integrin receptor specific it can specifically bind to integrin. In our invention, we designed a method for synthesizing a series of RGD-based bifunctional molecules to recruit antibodies. In general, DNP is coupled to RGD or a polypeptide or cyclic peptide thereof, which mediates immune killing and targets tumor cells by recruitment of antibodies against DNP.

The amino sequence of the cyclic RGD analogue in this invention is: Cyclo-(DFKRG) (SEQ ID NO:9). An embodiment of a synthetic RGD-DNP conjugate is as follows:

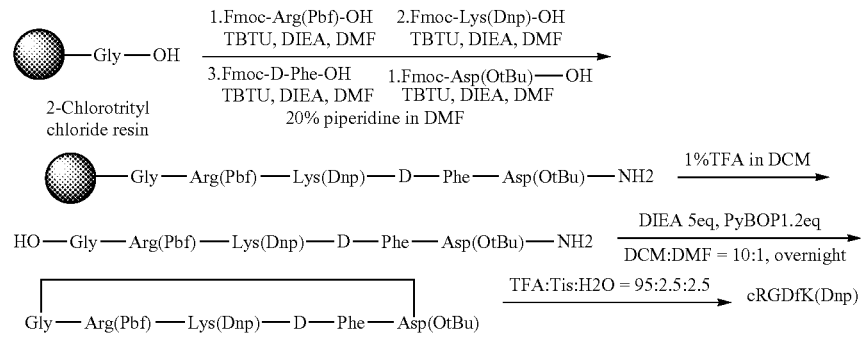

The implementation of the synthetic RGD-linker-DNP is as follows:

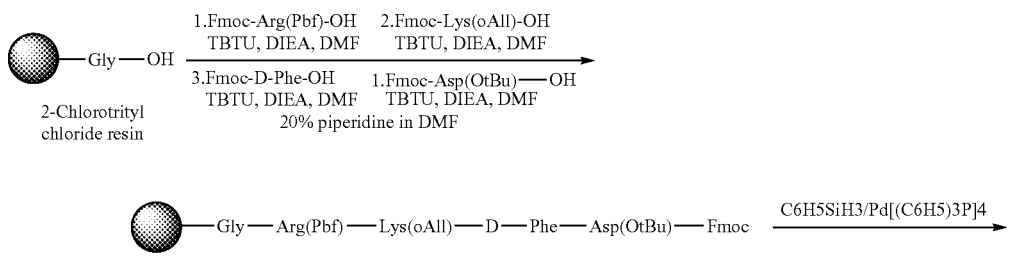

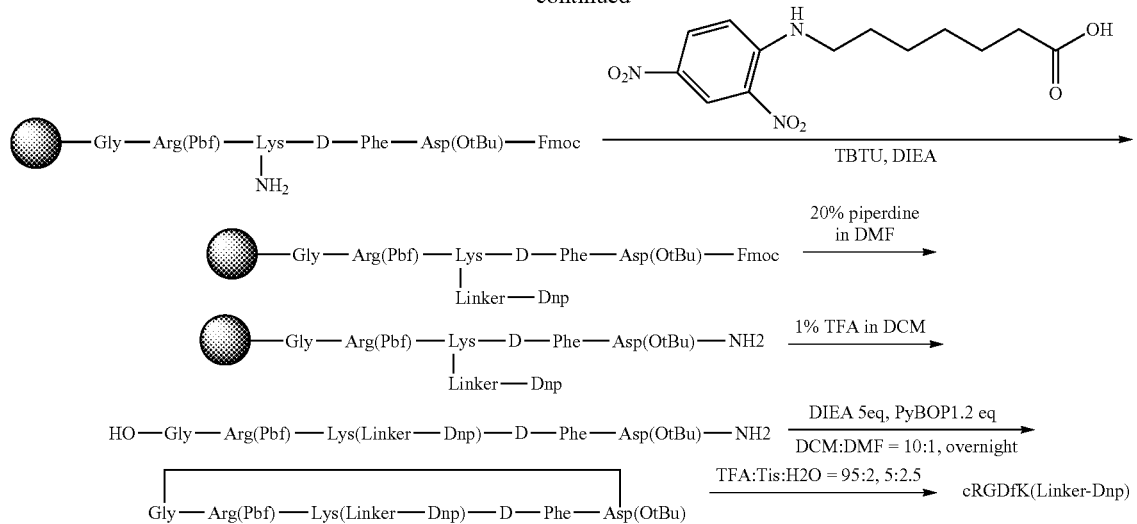

Figure 10:
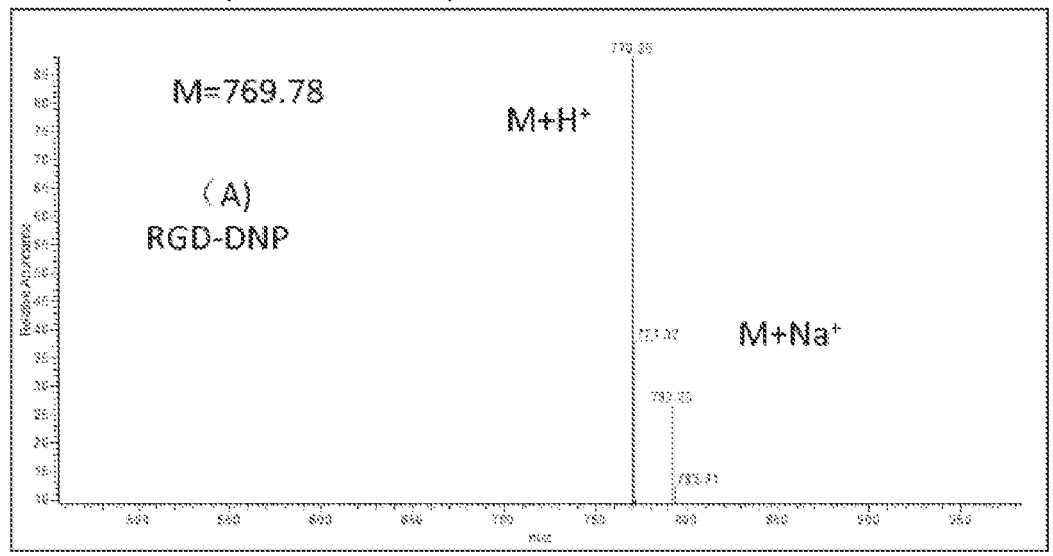
FIG. 10 provides the MS of RGD-NDP (A) and RGD-linker-DNP (B).
Figure 10:
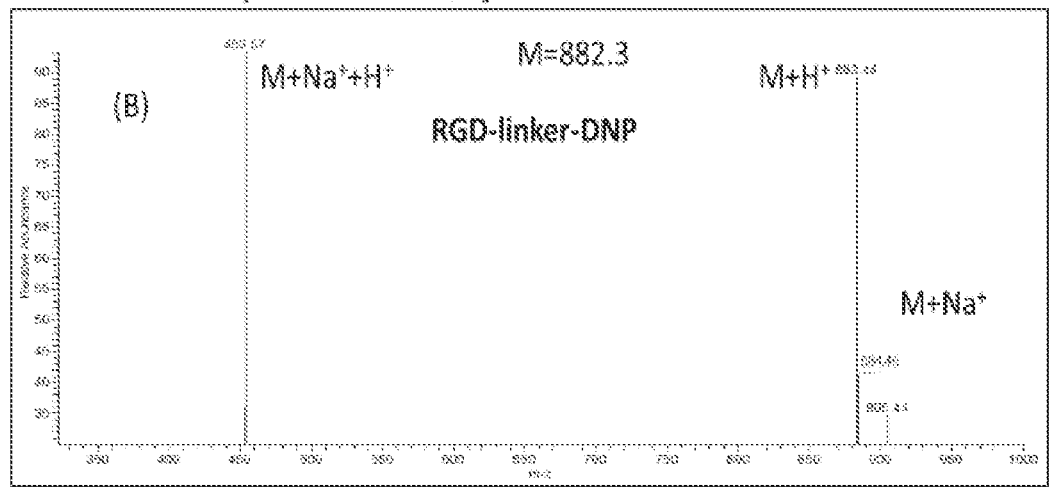

The synthesized compound was confirmed to be correct by mass spectrometry, and the mass spectrum is shown in FIG. 10. The actual molecular weight of RGD-DNP is 769.78, and 770.38 (M+H+) and 792.26 (M+Na+) appearing in the mass spectrum are consistent with the prediction; similarly the molecular weight of RGD-linker-DNP is 882.3, the mass ratio in the mass spectrum 453.57 (M+Na+H+) and 883.44 (M+H+) and 905.44 (M+Na+) are consistent with the prediction, indicating that the product is synthesized correctly.

The activity detection implementation for the compounds RGD-DNP and RGD-linker-DNP are as follows: including flow cytometry, CDC experiments, and ADCC experiments. The specific implementation scheme is as follows:

Cell assay implementation: cell culture: commercial cells HEK-293 (high expression of integrin αvβ3), SKOV-3 (high expression of integrin αvβ3, αvβ 5), and HT-29 (high expression of integrin αvβ5) was cultured in DMEM complete medium. All cell culture conditions were 37° C., 5% $CO_2$. Flow cytometry assay: ① The cells were digested with trypsin, resuspended in flow medium diluted to 1×105 cells. 400 μL of cells (40,000 cells) were added to a sterile EP tube. ② RGD analogues (SEQ ID NO:9), RGD-DNP and RGD-linker-DNP compounds were added at a final in all groups, incubate on ice for 1 h. Then the cells were washed and incubated with fluorescent secondary antibody for 0.5 h. ③ the cells were thoroughly washed gently with a flow buffer, resuspended, and analyzed by instruments.

ADCC assay implementation: ① HEK-293, SKOV-3, HT-29 cells were seeded in 96-well plates at a concentration of 10,000 cells/well. After the cells were fully attached, added with RGD analogues (SEQ ID NO:9), RGD-DNP and RGD-linker-DNP compounds at a final concentration of 250 nM and immediately added a certain concentration of anti-DNP antibody. ② After incubation for a period of time, freshly extracted PBMC cells were added at a certain effect target ratio for a certain period of time. ③ The supernatant was removed by centrifugation, and cytotoxicity was measured by the LDH method.

CDC assay implementation: ① HEK-293, SKOV-3, HT-29 cells were seeded in 96-well plates at a concentration of 5,000 cells/well. After the cells were fully attached, added with RGD analogues (SEQ ID NO:9), RGD-DNP and RGD-linker-DNP compounds at a final concentration of 250 nM and added a certain concentration of anti-DNP antibody at the same time. After 2 hours of incubation at 37° C., a final concentration of 10% of the complement solution was added and incubated for 1 hour at 37° C. After the incubation, the cell viability was measured by the cck8 method.

Figure 11:
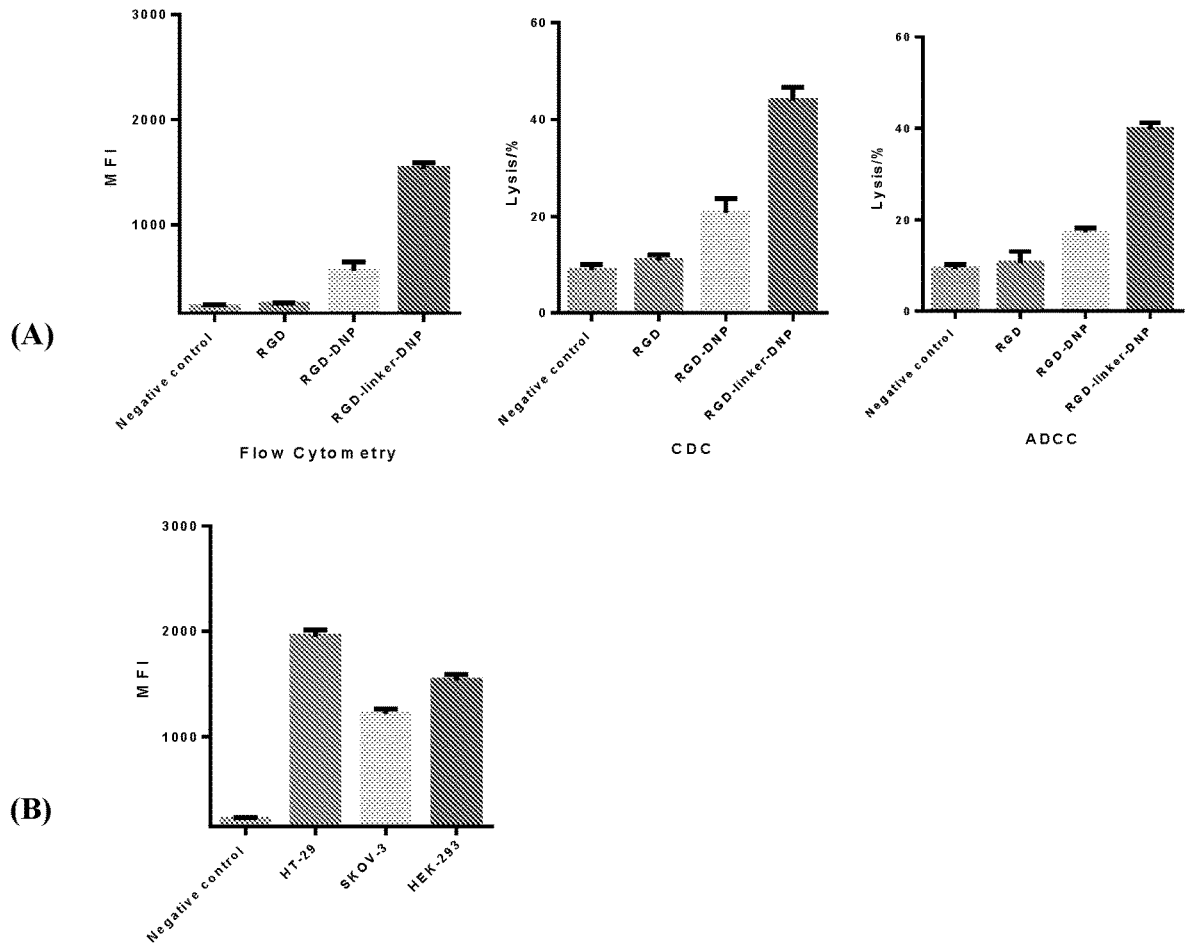
FIG. 11 provides (A): the flow cytometry (left picture), CDC (middle picture) and ADCC (right picture) assays of HEK-293 cells treated with PBS (negative control), RGD peptide RGD-DNP or RGD-linker-DNP. MFI: mean fluorescence intensity; and (B): the flow cytometry of SKOV3 cells treated with PBS (negative control), and HT-29, SKOV3, HEK-293 cells treated with RGD-linker-DNP. MFI: mean fluorescence intensity.

Flow cytometry, ADCC, CDC experimental results are shown in FIG. 11. The results show that both RGD-DNP and RGD-linker-DNP conjugated compounds can bind to HEK-293, SKOV-3 and HT-29 cells, but the binding ability to cells is slightly different. That probably because each cell expressed integrin is different. Both RGD-DNP and RGD-linker-DNP-conjugated compounds can recruit anti-DNP antibodies and target HEK-293 cells with high expression of integrin and mediate the immune response CDC and ADCC to further kill these cells. However, the immune killing effect mediated by these two compounds is different, the RGD-linker-DNP compound with a long connecting arm is more immune to cytotoxicity. According to the results, the long-lasting RGD-linker-DNP compound mediates the immune killing effect, which is consistent with the results of flow cytometry experiments (The CDC and ADCC kill rates of the short-lasting RGD-linker-DNP are 21% and 18%, and the CDC and ADCC kill rates of the long-lasting RGD-linker-DNP are 42% and 38%). This result indicates that the recruitment of DNP antibodies requires that the structure of DNP to be exposed outside the complex of RGD-integrin. If the linker is too short, it will affect the binding of anti-DNP antibodies to the RGD-integrin complex. In summary, our invention optimizes the length of a connecting arm.

What is claimed is:

1. A bi-functional compound having a chemical structure of formula I as follows:

wherein, A is dinitrophenol (DNP); and B is a 7D12 nanobody comprising the amino acid sequence of SEQ ID NO: 1 against a tumor cell epidermal growth factor receptor (EGFR) or a nanobody comprising the amino sequence of SEQ ID NO:2 against a human epidermal growth factor receptor 2 (HER2); $L_1$ and $L_2$ are linker linking A and B, wherein $L_1$ is polyethylene glycol (PEG); MULTICON is a multifunctional connector molecule or group;

MCON is 0; each n and n' is independently an integer from 1 to 15; NL1 is 1, and NL2 is 0, wherein n≥NL1, and n'≥NL2;

wherein the compound is 7D12-triEGDNP, having the chemical structure of formula I on which A is DNP, B is 7D12, $L_1$ is PEG3, or wherein the compound is HER2-hexEGDNP having the chemical structure of formula I on which A is DNP, B is HER2, $L_1$ is PEG6.

2. The compound according to claim 1, wherein each n and n' is independently an integer 2 to 6.

3. The compound according to claim 1 wherein the compound is 7D12-triEGDNP.

SEQUENCE LISTING

<160> NUMBER OF SEQ ID NOS: 9

<210> SEQ ID NO 1

<211> LENGTH: 155
<212> TYPE: PRT
<213> ORGANISM: Artificial Sequence
<220> FEATURE:
<223> OTHER INFORMATION: The EGFR-specific nanobody 7D12 sequence was genetically engineered to contain at its C-terminus a sorting signal for further sortase A-mediated ligation.

<400> SEQUENCE: 1

```
Met Ala Gln Val Lys Leu Glu Glu Ser Gly Gly Gly Ser Val Gln Thr
1               5                   10                  15

Gly Gly Ser Leu Arg Leu Thr Cys Ala Ala Ser Gly Arg Thr Ser Arg
            20                  25                  30

Ser Tyr Gly Met Gly Trp Phe Arg Gln Ala Pro Gly Lys Glu Arg Glu
        35                  40                  45

Phe Val Ser Gly Ile Ser Trp Arg Gly Asp Ser Thr Gly Tyr Ala Asp
    50                  55                  60

Ser Val Lys Gly Arg Phe Thr Ile Ser Arg Asp Asn Ala Lys Asn Thr
65                  70                  75                  80

Val Asp Leu Gln Met Asn Ser Leu Lys Pro Glu Asp Thr Ala Ile Tyr
                85                  90                  95

Tyr Cys Ala Ala Ala Gly Ser Ala Trp Tyr Gly Thr Leu Tyr Glu
            100                 105                 110

Tyr Asp Tyr Trp Gly Gln Gly Thr Gln Val Thr Val Ser Ser Ala Ala
        115                 120                 125

Ala Glu Gln Lys Leu Ile Ser Glu Glu Asp Leu Asn Gly Ala Ala Leu
    130                 135                 140

Pro Glu Thr Gly Gly His His His His His
145                 150                 155
```

<210> SEQ ID NO 2
<211> LENGTH: 130
<212> TYPE: PRT
<213> ORGANISM: Artificial Sequence
<220> FEATURE:
<223> OTHER INFORMATION: The HER2-specific nanobody C7b sequence was genetically engineered to contain at its C-terminus a sorting signal for further sortase A-mediated ligation.

<400> SEQUENCE: 2

```
Met Gln Val Gln Leu Val Gln Ser Gly Gly Gly Leu Val Gln Ala Gly
1               5                   10                  15

Gly Ser Leu Arg Leu Ser Cys Ala Ala Ser Gly Arg Thr Phe Ser Ser
            20                  25                  30

Tyr Ala Met Ala Trp Phe Arg Gln Ala Pro Gly Lys Glu Arg Glu Phe
        35                  40                  45

Val Ala Ala Ile Ser Trp Ser Gly Ala Asn Ile Tyr Val Ala Asp Ser
    50                  55                  60

Val Lys Gly Arg Phe Thr Ile Ser Arg Asp Asn Ala Lys Asp Thr Val
65                  70                  75                  80

Tyr Leu Gln Met Asn Ser Leu Lys Pro Glu Asp Thr Ala Val Tyr Tyr
                85                  90                  95

Cys Ala Val Lys Leu Gly Phe Ala Pro Val Glu Glu Arg Gln Tyr Asp
            100                 105                 110

Tyr Trp Gly Gln Gly Thr Gln Val Thr Val Ser Ser Leu Pro Glu Thr
        115                 120                 125

Gly Gly
    130
```

```
<210> SEQ ID NO 3
<211> LENGTH: 10
<212> TYPE: PRT
<213> ORGANISM: Artificial Sequence
<220> FEATURE:
<223> OTHER INFORMATION: Solid phase synthesis.
<220> FEATURE:
<221> NAME/KEY: MOD_RES
<222> LOCATION: (1)..(1)
<223> OTHER INFORMATION: (p)Glu
<220> FEATURE:
<221> NAME/KEY: MOD_RES
<222> LOCATION: (6)..(6)
<223> OTHER INFORMATION: Lys(N3)

<400> SEQUENCE: 3

Glu His Trp Ser Tyr Lys Leu Arg Pro Gly
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Solid phase synthesis.

<400> SEQUENCE: 4

Cys Tyr Gly Gly Arg Gly Asn Gly
1               5

<210> SEQ ID NO 5
<211> LENGTH: 13
<212> TYPE: PRT
<213> ORGANISM: Artificial Sequence
<220> FEATURE:
<223> OTHER INFORMATION: Solid phase synthesis.

<400> SEQUENCE: 5

Cys Asn Gly Arg Cys Val Ser Gly Cys Ala Gly Arg Cys
1               5                   10

<210> SEQ ID NO 6
<211> LENGTH: 19
<212> TYPE: PRT
<213> ORGANISM: Artificial Sequence
<220> FEATURE:
<223> OTHER INFORMATION: Solid phase synthesis.

<400> SEQUENCE: 6

Gly Asn Gly Arg Gly Gly Val Arg Ser Ser Ser Arg Thr Pro Ser Asp
1               5                   10                  15

Lys Tyr Cys

<210> SEQ ID NO 7
<211> LENGTH: 8
<212> TYPE: PRT
<213> ORGANISM: Artificial Sequence
<220> FEATURE:
<223> OTHER INFORMATION: Solid phase synthesis.

<400> SEQUENCE: 7

Gly Gly Gly Cys Asn Gly Arg Cys
1               5

<210> SEQ ID NO 8
<211> LENGTH: 8
<212> TYPE: PRT
```

```
<213> ORGANISM: Artificial Sequence
<220> FEATURE:
<223> OTHER INFORMATION: Solid phase synthesis.
<220> FEATURE:
<221> NAME/KEY: misc_feature
<222> LOCATION: (4)..(8)
<223> OTHER INFORMATION: Cyclic

<400> SEQUENCE: 8

Gly Gly Gly Cys Asn Gly Arg Cys
1               5

<210> SEQ ID NO 9
<211> LENGTH: 5
<212> TYPE: PRT
<213> ORGANISM: Artificial Sequence
<220> FEATURE:
<223> OTHER INFORMATION: Solid phase synthesis.
<220> FEATURE:
<221> NAME/KEY: misc_feature
<222> LOCATION: (1)..(5)
<223> OTHER INFORMATION: Cyclic

<400> SEQUENCE: 9

Asp Phe Lys Arg Gly
1               5
```